United States Patent
Rastogi

(10) Patent No.: US 10,573,412 B2
(45) Date of Patent: Feb. 25, 2020

(54) PATIENT-CENTERED MOBILE COMMUNICATION SYSTEM AND METHOD

(71) Applicant: Sanjeev Rastogi, Munster, IN (US)

(72) Inventor: Sanjeev Rastogi, Munster, IN (US)

( * ) Notice: Subject to any disclaimer, the term of this patent is extended or adjusted under 35 U.S.C. 154(b) by 974 days.

(21) Appl. No.: 14/817,602

(22) Filed: Aug. 4, 2015

(65) Prior Publication Data
US 2016/0034654 A1 Feb. 4, 2016

Related U.S. Application Data

(60) Provisional application No. 62/032,877, filed on Aug. 4, 2014.

(51) Int. Cl.
G16H 40/63 (2018.01)
(52) U.S. Cl.
CPC .................... *G16H 40/63* (2018.01)
(58) Field of Classification Search
CPC ........ G06F 19/34; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | |
|---|---|---|---|
| 2007/0067182 A1 | 3/2007 | Harp et al. | |
| 2007/0067183 A1 | 3/2007 | Harp et al. | |
| 2007/0067184 A1 | 3/2007 | Harp et al. | |
| 2012/0310666 A1* | 12/2012 | Xu | G06F 19/00 705/3 |
| 2013/0065569 A1* | 3/2013 | Leipzig | G06F 9/453 455/416 |

OTHER PUBLICATIONS

Comstock, Jonah, "Hearst Health Acquires Care Transition Software Maker CareInSync," http://mobihealthnews.com/32462/hearst-health-acquires-care-transition-software-maker-careinsync/, Apr. 24, 2014, 10 pages.

(Continued)

*Primary Examiner* — Linh Giang Le
(74) *Attorney, Agent, or Firm* — Ware, Fressola, Maguire & Barber LLP

(57) ABSTRACT

A patient-centered mobile communication system and method that includes a physician's main menu comprising a processor, a memory including computer program code, the memory and the computer program code configured to, with the processor, cause the system at least to perform a physician main menu with at least one selectable button (region) to view patient information regarding at least one patient for which a physician provide care, at least one selectable button (region) to view the identity of one or more physicians also providing care to said at least one patient, and at least one selectable button (region) to communicate with any one of the identified physicians.

20 Claims, 47 Drawing Sheets

(56) References Cited

OTHER PUBLICATIONS

"Zynxcarebook, HIPAA-Compliant Secure Messaging and Care Coordination," http://www.zynxhealth.com/Solutions/Zynx-Carebook, Nov. 4, 2014, 3 pages.

"Zynx Health Unveils Revolutionary Evidence-Based Mobile Care Team Coordination and Secure Messaging Solution," http://www.prnewswire.com/news-releases/zynx-health-unveils-revolutionary-evidence-based-mobile-care-team-coordination-and-secure-messaging-solution-275990351.html, Sep. 22, 2014, 3 pages.

* cited by examiner

PATIENT-CENTERED MOBILE COMMUNICATION SYSTEM AND METHOD

CROSS REFERENCE TO RELATED APPLICATIONS

The present application claims the benefit of U.S. Provisional Patent Application No. 62/032,877, filed on Aug. 4, 2014, which is hereby incorporated by reference in its entirety.

TECHNICAL FIELD

The present invention relates to a communication system and method and, in particular, a communication system and method for medical patients and their attending physicians.

BACKGROUND OF THE INVENTION

Today, health care is a team sport where multiple providers work in concert to care for patients. In order to deliver timely, cost-effective, quality care, it is imperative that the health care team be enabled to communicate promptly and efficiently. In the hospital setting, communication between providers is centered on the hospital-based electronic health record (EHR). It is often facilitated through hospital staff, but in itself can be time-consuming and incomplete. When the patient leaves the hospital, this communication becomes even more limited, because in an outpatient setting, health information is compartmentalized into each physician's individual practice-EHR. This limitation can pose serious risks to patient safety, and requires that healthcare providers quickly communicate key decisions regarding patient care amongst each other. However it can be tedious and time consuming to identify, let alone contact, another healthcare provider involved in the care of an individual patient. Current inefficiencies in communication have thus created a potential for lapses in patient-care, leading to treatment errors, and has become a major source of dissatisfaction among healthcare providers and patients.

SUMMARY OF THE INVENTION

A patient-centered mobile communication (PCMC) system and method according to the present invention, helps to fill this gap in communications by providing a mobile system and method that enables patient-centered doctor-to-doctor communications, allowing patients and their providers to view names and contact information of all healthcare providers treating a particular patient, a patient's scheduled appointments, and key healthcare information, in a manner compliant with the Health Information Portability and Accountability Act (HIPAA) privacy rules and consistent with the Health Language 7 (HL7—see www.hl7.org) platform.

The system and method of the present invention allow a patient using a computing or mobile device to identify and link to their healthcare providers, as well as to send the healthcare providers messages, which are otherwise typically constrained by healthcare practice parameters. It also allows the patient to review their medical information and to create a health calendar for appointments, among other functionalities.

Healthcare providers, by use of an application forming part of the present invention, can identify their patients, as well as link to a network of healthcare providers that jointly care for a specific patient in a list of patients associated with another healthcare provider. Healthcare providers can also identify how many patients they share with other healthcare providers in their network, and thus can focus their resources on particular network-relationships as required.

Furthermore, a healthcare provider can easily communicate with another healthcare provider by a simple one-click step. This creates a simple and effective manner for communicating with these other healthcare providers who are all treating the same patient. In particular, a healthcare provider through use of an application forming part of the present invention can choose from a number of choices for communicating with other healthcare providers, including text messages, telephone communications and the like. In addition, if a particular method for communicating with another healthcare provider is unsuccessful, the system and method can trigger a "tickler" or reminder which provides a reminder to the healthcare provider to reconnect with the healthcare provider for whom they have been unsuccessful in their earlier communication attempts.

Thus, the present invention provides a system and method which serves as a patient-centered, doctor-to-doctor system and methodology where the healthcare provider can see in their network the other healthcare providers that are centered around (that is, provide healthcare services to) each individual patient and thereby optimize the care provided by each individual healthcare provider through coordinated and improved patient-centered physician-to-physician communication. The system and method can also provide HIPAA-protected key health information to a patient wherever that patient travels around the world which can then be used by healthcare providers that are linked to the network as needed.

Furthermore, due to the mobile nature of the applications associated with the present invention, a technology platform is provided that allows physicians to communicate with other physicians while the physicians are "on the move" without requiring the physicians to use a particular location, such as a kiosk or office in order to obtain contact information of another physician. The present invention therefore provides flexibility to physicians who are constantly on the move and seeing patients across different healthcare settings, including hospitals, nursing homes, dialysis facilities, outpatient clinics, etc.

The present invention also improves patient-physician workflow, decreases gaps in healthcare due to communication issues, reduces frustrations and missed opportunities and leads to a proactive and coordinated management of a healthcare provider's patients.

The present invention is a different approach from that of other physician or healthcare practice networking tools. Prior art applications, such as Docbook, essentially function as contact lists and provide physicians belonging to a given group or society the ability to communicate with each via their mobile devices. Such applications do not include any patient component and thus fail to identify patient-physician networks to enable patient centered communications and are also unable to link patient information to a communication tool. Thus, these prior art devices are unable to reveal a physician's networking information to indicate the level of interaction between healthcare providers through patient care.

The present invention thereby provides a system and method that greatly facilitates communication between physicians and other healthcare providers concerning their common patients, as well as to provide healthcare providers with the ability to join other healthcare provider networks and thereby show common patients among various healthcare providers (link or level 0), as well as patients which, although not directly common between two healthcare providers, are nevertheless linked at a higher level (such as link level 1 and link level 2 as explained more fully below).

According to a first aspect of the invention, a patient-centered mobile communication system is provided. The system comprises a server comprising a processor, and a memory. The system further comprises at least one physician mobile device comprising a processor and a memory including computer program code. The memory and the computer program code are configured to, with the processor, cause the at least one physician mobile device at least to perform displaying a physician main menu with at least one selectable button to view patient information regarding at least one patient for which a physician provides care, displaying at least one selectable button to view the identity of one or more physicians also providing care to the at least one patient, and displaying at least one selectable button to communicate with any one of the identified physicians. The system further comprises at least one patient mobile device comprising a processor and a memory including computer program code. The memory and the computer program code are configured to, with the processor, cause the at least one patient mobile device at least to perform displaying a patient main menu with at least one selectable button to view patient information and identified physicians for the patient; and displaying at least one selectable button to communicate with any one of the identified physicians for the patient.

According further to the first aspect of the invention, each of the at least one selectable buttons to communicate with any one of the identified physicians includes specific buttons associated with specific type of communication techniques. The specific types of communications can include telephone communication, video communication, text message communication, scheduled future communications, and prior communication information.

According further to the first aspect of the invention, the at least one physician mobile device is further configured to identify all of the common patients between two physicians. The at least one physician mobile device is further configured to display third party patient information to the physician associated with the system and information generated by the patient to the physician associated with the at least one physician mobile device. A degree of linking between the physician associated with the system and other physicians can be provided, wherein the degree of linking includes common/shared patients, non-common patients that are linked to at least one other physician who is linked to the physician associated with the system, and patients linked by other physicians linked to the physician associated with the system.

According further to the first aspect of the invention, the server, the at least one physician mobile device, and the at least one patient mobile device each comprise at least one transmitter and at least one receiver, and wherein the server is configured to send and receive information to and from each of the at least one physician mobile device and the at least patient mobile device.

According to a second aspect of the invention, a method for providing a patient-centered mobile communication system to a user having a mobile device is provided. The method comprises providing a medical information and communication application to a user for installation on a mobile device, the mobile device comprising a memory configured to store the application, a processor configured to execute the application, a display configured to display the executed application, a user interface configured to allow the user to operate the executed application, a transmitter and a receiver. The method further comprises providing medical information pertaining to the user and storing the medical information on a server comprising a processor and a memory; wherein access to the stored medical data is restricted to the user and linked third party users. A request from the user mobile device is transmitted to the server for the medical information to be transmitted to the user mobile device. The medical information is received by the mobile device for viewing by the user in the application on the mobile device. The method further comprises generating a link request from the user and transmitting the link request to a second user having a second mobile device, wherein the link request is a request that the second user become a linked third party user, and receiving a verification of acceptance of the link request by the second user and authorizing the second user to become a linked third party user, wherein the second user can access the medical information via the application executed on the mobile device of the second user.

According further to the method of the second aspect of the invention, the linked third party users include a plurality of physicians or health professionals, and the medical information comprises a list of the linked third party users. The method may further comprise receiving by the user mobile device updates to the medical information made by one or more linked third party users. The method may also further comprise sending and/or receiving communications within the application executed on the mobile device, to or from one or more of the linked third party users.

According to a third aspect of the invention, a method for providing a patient-centered mobile communication system to a user having a mobile device is provided. The method comprises providing a medical information and communication application to a user for installation on a mobile device, wherein the mobile device comprises a memory configured to store the application, a processor configured to execute the application, a display configured to display the executed application, a user interface configured to allow the user to operate the executed application, a transmitter and a receiver. The method further comprises providing medical information pertaining to a patient and storing the medical information on a server comprising a processor and a memory; wherein access to the stored medical data is restricted to the patient and linked third party users. A link request from the user is generated and transmitted to the patient having a second mobile device, wherein the link request is a request that the user become a linked third party user. A verification of acceptance of the link request by the patient is received, authorizing the user to become a linked third party user. The method further comprises transmitting a request from the user mobile device to the server for the medical information to be transmitted to the user mobile device; and receiving the medical information by the mobile device for viewing by the user in the application on the mobile device.

According further to the method of the third aspect of the invention, the linked third party users include a plurality of physicians or health professionals, and the medical information received by the user comprises a list of the linked third party users. The method may further comprise sending and/or receiving communications within the application executed on the mobile device, to or from the patient, and sending and/or receiving communications within the application executed on the mobile device, to or from one or more of the linked third party users. The method may further comprise scheduling an event or notification relating to the patient, and transmitting a reminder message relating to the event or notification to the second mobile device at the scheduled time.

According further to the method of the third aspect of the invention, the method may further comprise generating a plurality of further link requests from the user and transmitting the link requests to a plurality of further patients, each having a mobile device, and receiving a verification of acceptance of one or more of the plurality of link requests by one or more of the plurality of further patients and authorizing the user to become a linked third party user for the one or more of the plurality of further patients. The user thus becomes a linked third party user for a plurality of patients, each having medical information stored on the server. The method may further comprise receiving information within the application relating to one or more of the plurality of physicians or health professionals, including a list of patients who have authorized both the user and the one or more of the plurality of physicians or health professionals to be linked third party users.

According further to the method of the third aspect of the invention, the method may further comprise updating the medical information for the patient and transmitting the updated medical information to the server and receiving updated medical information from the server, which has been updated by the patient or another linked third party user.

DETAILED DESCRIPTION OF THE FIGURES

The present invention will now be described, with reference made to FIGS. 1-25G.

Figures 1, 2:
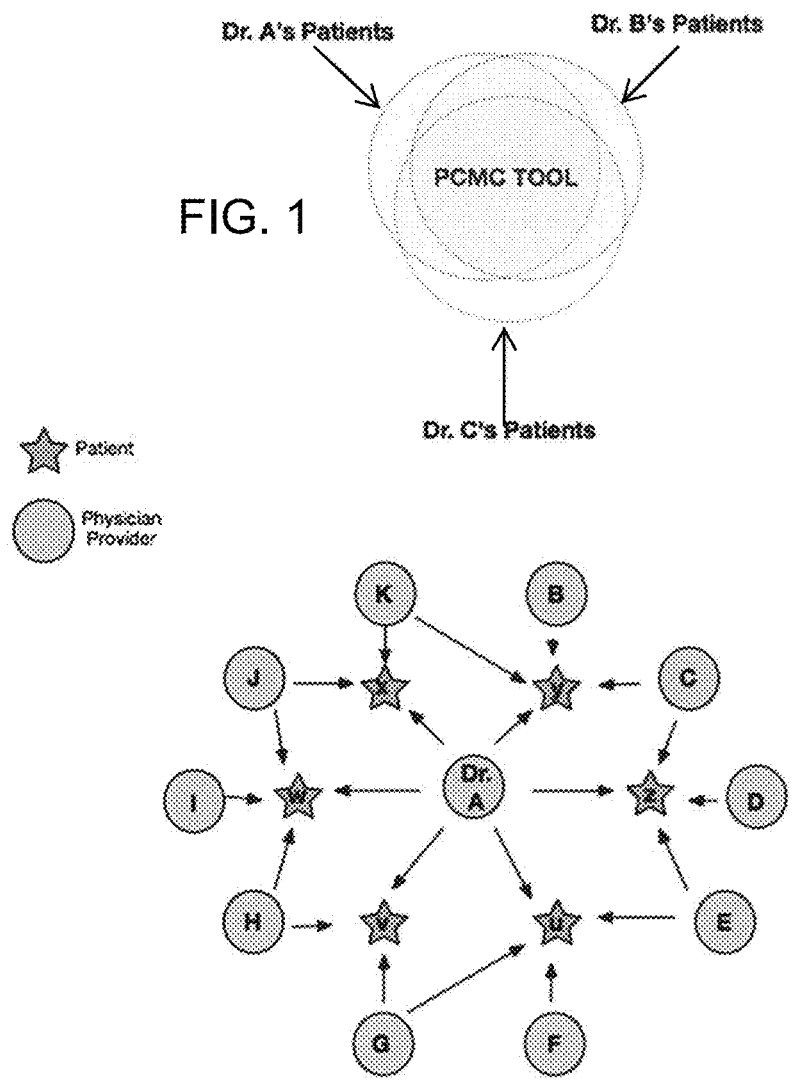
FIG. 1 is a Venn type drawing showing how a typical patient's care is shared between multiple physicians.
FIG. 2 is a diagram showing patient centered mobile communications according to the present invention which links each healthcare provider to their patients and patients to their healthcare providers.

FIG. 1 shows a typical healthcare situation where patients of one healthcare provider (the terms "healthcare providers", "physicians" and "doctors" are used as equivalent terms herein although healthcare providers can potentially include non-physician healthcare providers) overlap to some extent with patients of other healthcare providers. Thus, it is seen, for example, that patients of Dr. A, represented by a circle in a Venn diagram, intersect to a degree with patients of Dr. B, as well as patients of Dr. C, both also represented by circles in the Venn diagram. The present invention thereby provides a system and method (sometimes referred to in the drawings as a "patient centered mobile communication (PCMC) tool") to facilitate communications between healthcare providers for the shared patients of two or more physicians.

Thus, as is explained more fully below, information regarding common patients between, for example, Drs. A and B can be communicated between the doctors in accordance with the invention. These communications thus allow each doctor to not only know the identity of other doctors providing healthcare for that patient, but allow for patient-specific communications between these doctors so as to help coordinate care for that particular patient.

FIG. 2 is an example of a typical complex patient provider network where each patient receives care from multiple healthcare providers and each provider furnishes care to multiple patients. This example includes Doctors A, B, C, D, E, F, G, H, I J and K and Patients u, v, w, x, y and z, which share doctor-patient relationships between them. The present invention is able to link each healthcare provider to their patients and patients to their healthcare providers, as well as to link healthcare providers to other healthcare providers that provide care to shared patients so that each healthcare provider can determine which other healthcare providers are linked to a given patient.

Figure 3:
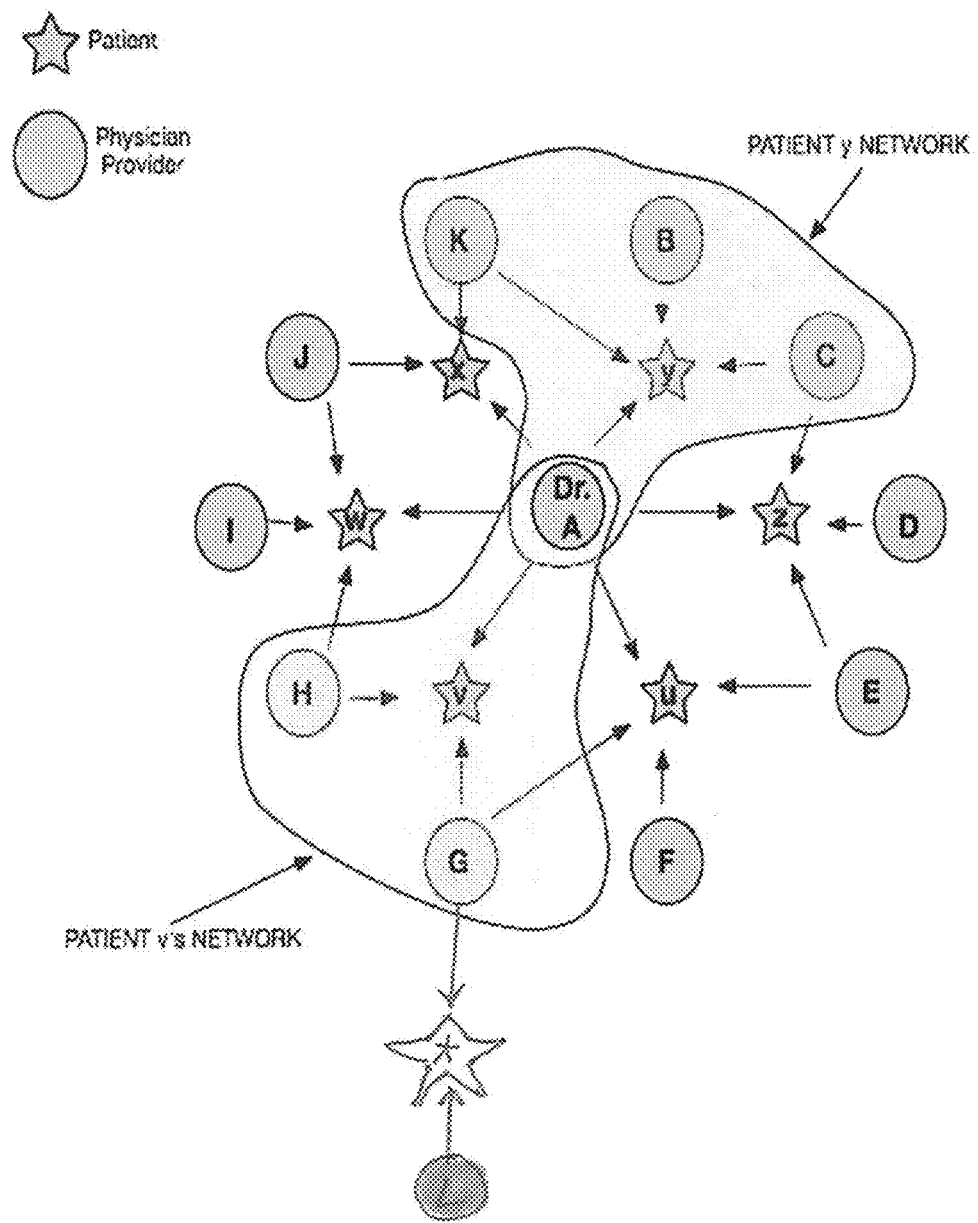
FIG. 3 is an example where healthcare providers (doctors A, K, B and C) can find other healthcare providers who provide care to a particular patient (patient y), such as doctors A, H and G can find each other through use of the present invention.

FIG. 3 is an example of how healthcare providers associated with a particular patient (for example, patient y) can find the identity of other healthcare providers providing care to that patient and also allows each healthcare provider to determine how many patients that healthcare provider shares with another healthcare provider. For example, Drs. A and K share two patients, namely patients x and y, while Drs. J and E do not share any patients. Thus, the implementation of the present invention allows for a physician to identify and contact other healthcare providers associated with a particular patient.

Figure 4:
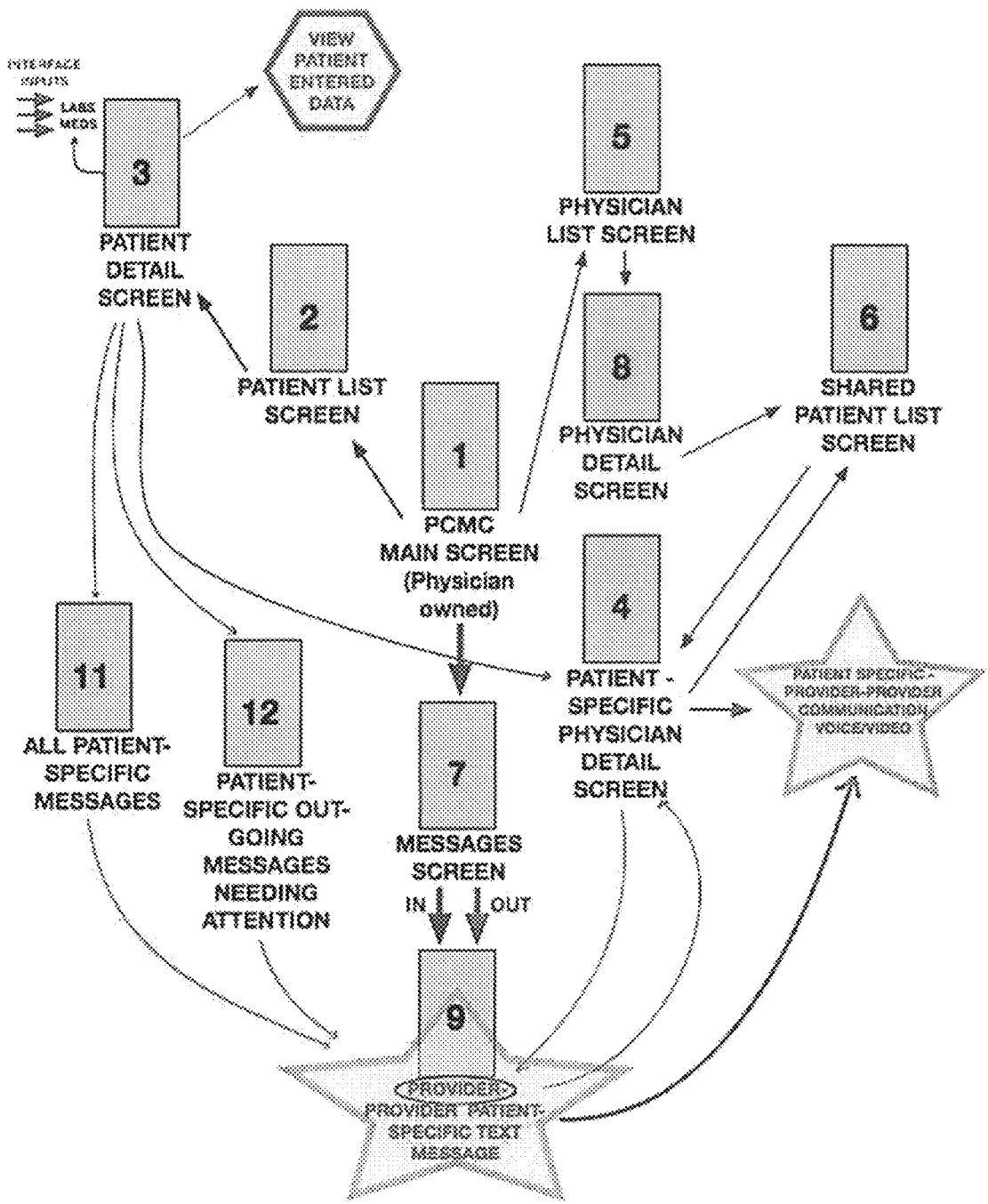
FIG. 4 is a flow chart showing operation of a first embodiment of the present invention and, in particular, various application screens that are seen on the physician-side implementation of the present invention.

FIG. 4 is an overall flow diagram for the physician side implementation (also called "physician owned" in the drawings) of the present invention. All of the various screens (Screens 1-12) that are available in the physician application of the present invention are shown in FIGS. 6-17, and described more fully below.

The application in accordance with the invention incorporates security and authentication rules to protect the confidentiality of the users' medical data. On the physician's side, a physician ("Physician A") can enroll with an assigned username and password provided to him or her by a subscribing organization, which can be authenticated with a database kept in a Carelogic application. Physician A may enroll him or herself with his or her name, address, NPI number and an authenticated email, which is verified by the state medical society. No provider enrolled in the application may view any patient's information without a link to that patient Once Physician A is enrolled, another physician using the application ("Physician B") may send a link to allow Physician A to join a patient's network (to which Physician B already belongs), or Physician B's network. Physician A may also connect to a patient by a link sent by a subscribing organization using the application. Physician A also may join a patient's network via a link authorized by the patient. Once enrolled, in each instance the user physician/provider accesses the application, the user will be required to follow secure password authentication and the user's credentials will be authenticated through an OAuth service when a secure server database is accessed for patient information, whether data is housed in a Carelogic database, or via a FHIRE API to an electronic data repository. An audit log will be maintained of all links and the metadata associated with the link.

Figure 5:
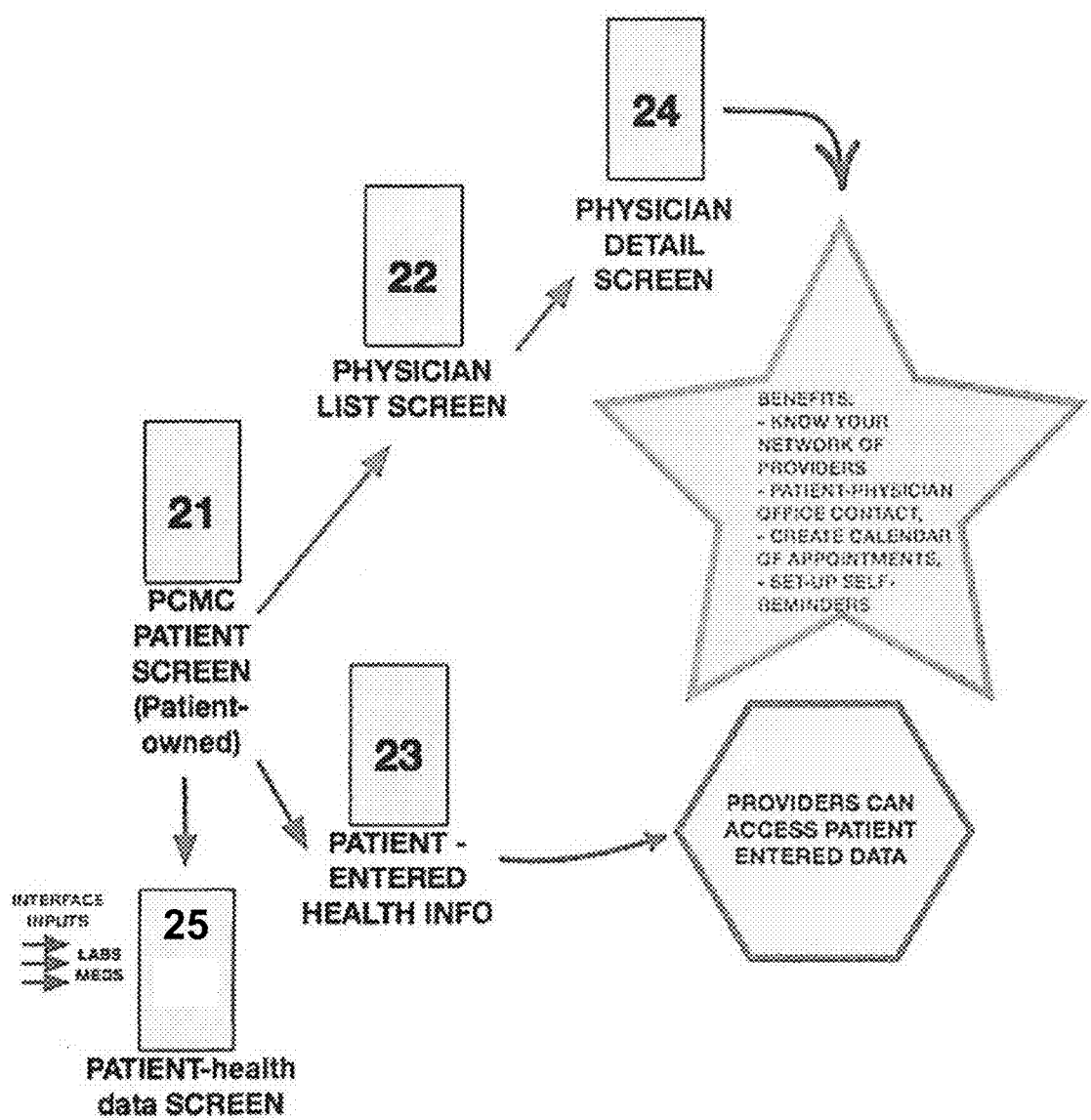
FIG. 5 is a flow chart showing operation of a first embodiment of the present invention and, in particular, various application screen from the patient-side implementation of the present invention.

On the patient side of the application, the patient may enroll through an email address and password supplied by a subscribing organization. The patient may enroll by entering their identification details, such as first name, last name, date of birth, address, social security number, email, and chosen secure password. Any potential duplication of patient entry will be identified and given for resolution to subscribing organization, or PCP before access can be granted, via a password reset mechanism. A patient's access to data through the patient side of the application is restricted by the user patient's secure user name and password. A user's credentials will be authenticated through an OAuth service every time the secure server database is accessed for patient information, whether data is housed in a Carelogic database, or via a FHIRE API to an electronic data repository In a similar manner, FIG. 5 is an overall flow chart of the patient-side implementation of the present invention. This flow chart shows various screens and actions that can be taken by a patient using a patient application (patient owned) according to the present invention. All of the various screens (Screens 21-25) that are available in the patient application of the present invention are shown in FIGS. 8-22, and described more fully below.

The various screen shots for different actions taken relative to the flow charts shown in FIGS. 4 and 5 are presented in FIGS. 6-22. These typical screen shots are examples of the information presented to the physician for the physician-owned application and to the patient for the patient-owned application, as well as what actions may be selected.

Figure 6:
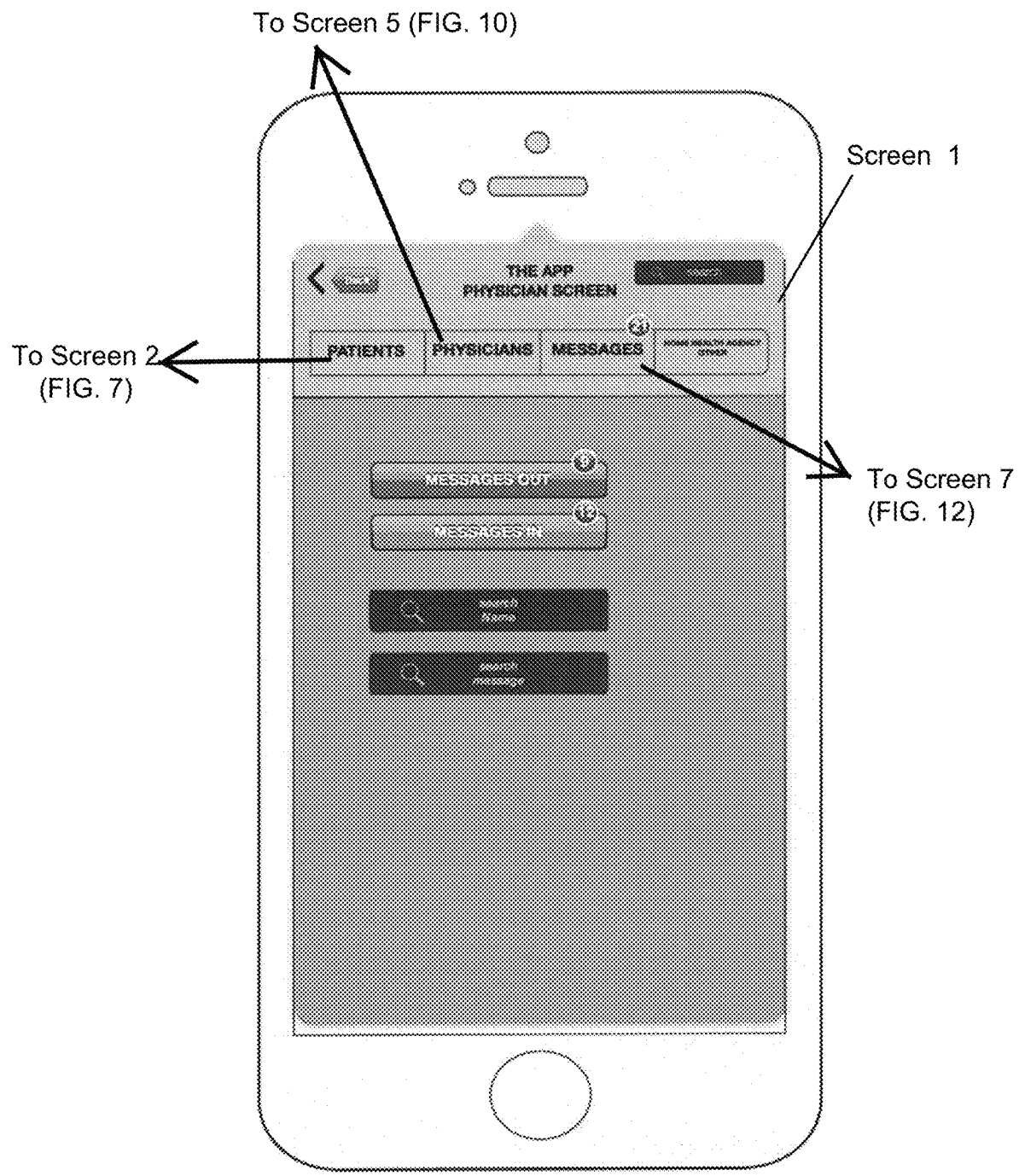
FIG. 6 is a screen shot (Screen 1) regarding the main physician screen for an application according to the present invention used by a physician (healthcare provider).

FIG. 6 (Screen 1) shows the main physician owned screen, which is the main screen or home screen for the portion of the present invention operated by a physician or other healthcare provider. As seen in FIG. 6, various options are available, including a PATIENTS button (leading to Screen 2 (FIG. 7)), a PHYSICIANS button (leading to Screen 5 (FIG. 10)), a MESSAGES button (leading to Screen 7 (FIG. 12)), and a HOME HEALTH AGENCY OTHER button, which shows linked nursing homes or other home health agency contacts. MESSAGES-OUT and MESSAGES-IN buttons are provided to access the physician's outgoing and incoming messages. A SEARCH BY NAME button leads to a search of patients, physicians and other providers by name, a SEARCH BY MESSAGE button leads to a search of all messages, and a SEARCH button allows for a global search. For the MESSAGES-OUT button, the number in a circle represents the number of outgoing messages generated, while for the MESSAGES-IN button the number in a circle represents the number of incoming messages and in the MESSAGES button the total number of outgoing and incoming messages are shown in the number in a circle.

Figure 7:
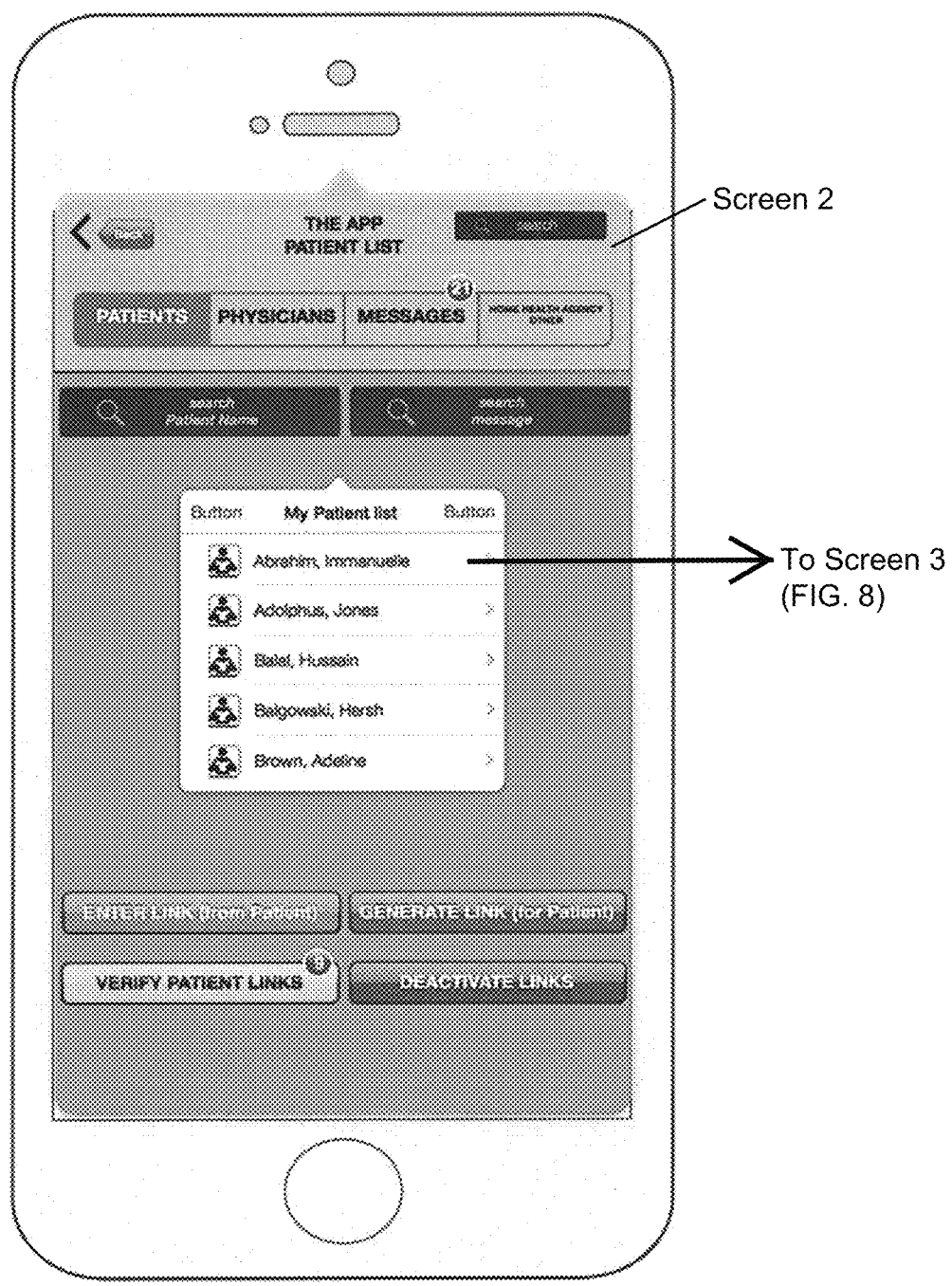
FIG. 7 is a screen shot (Screen 2) showing the list of patients associated with a particular physician, and other options available including reading of messages, as well as the number of unread messages.
Figure 8:
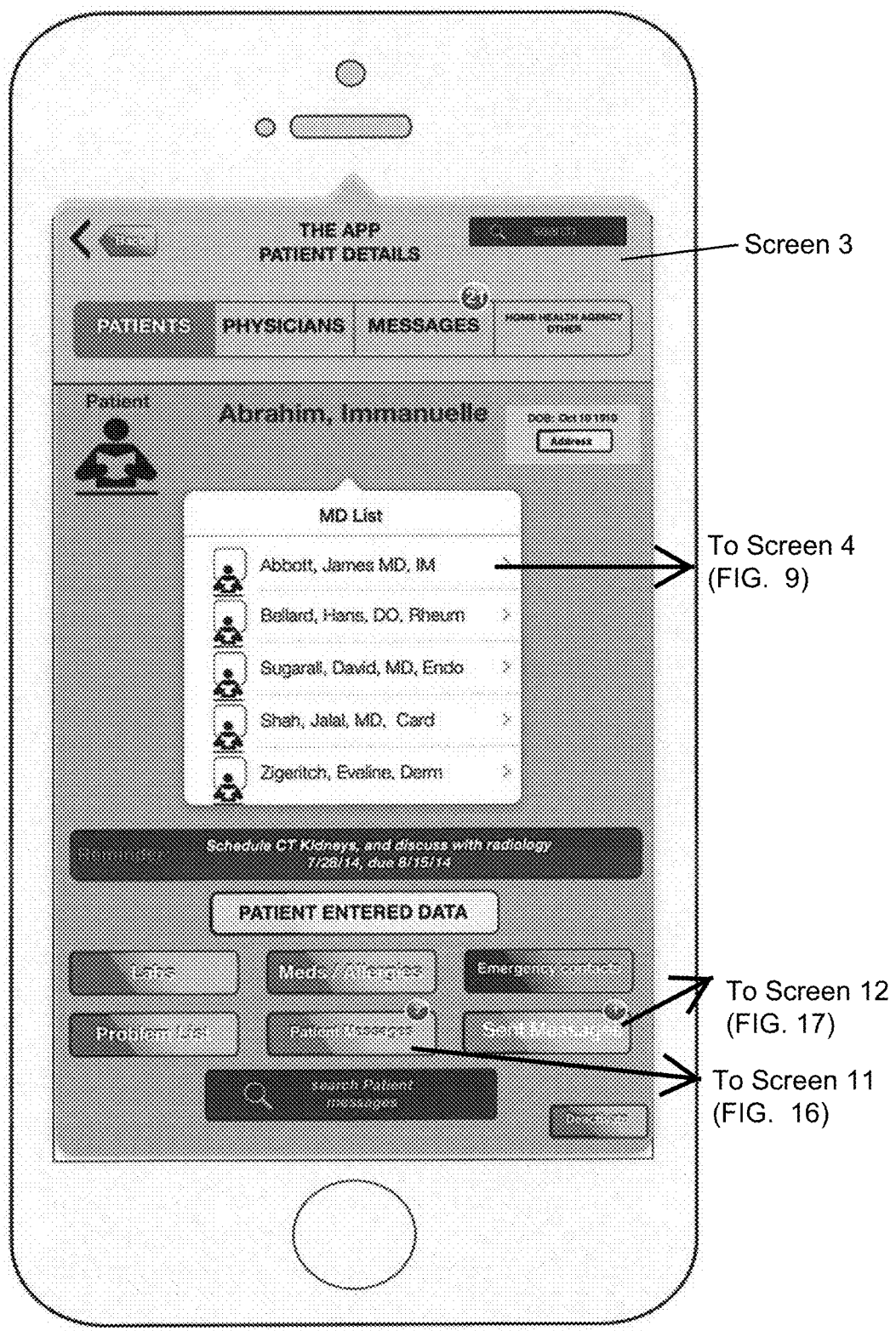
FIG. 8 is a physician owned patient details physician list screen shot (Screen 3) for a particular physician's patient and illustrating other physicians that provide care for that particular patient.

FIG. 7 (Screen 2) is the patient list screen which from the main screen occurs when the PATIENTS button is selected. The patient list screen lists all of the patients associated with this particular physician. The patients are listed in the middle of the screen and this list is scrollable. For any particular patient, selection of that patient provides details of that patient, such as shown in Screen 3 (FIG. 8). FIG. 7 also shows an ENTER LINK (from Patient) button which allows the physician to enter a link associated with a patient already in the network of the system but not the physician's personal network within the system, by a patient generated invitation or code. This will allow the patient to become part of the physician's network of patients in the system. A GENERATE LINK (for Patient) button is provided which allows the physician to generate a link-code to provide to a particular patient who is not in the physician's network. This allows the patient to join the physician's network, which gives the physician access to the patient's data. The physician may verify link requests in progress from patients and other physicians with the VERIFY PATIENT LINKS button and deactivate links that are no longer active, such as for patients or physicians who have moved out of the area, via a DEACTIVATE LINKS button. The SEARCH PATIENT NAME button and a SEARCH MESSAGE button are also provided in addition to the main buttons, that is the PATIENTS, PHYSICIANS, MESSAGES and HOME HEALTH AGENCY OTHER buttons, as well as the GENERAL SEARCH button.

Figure 9:
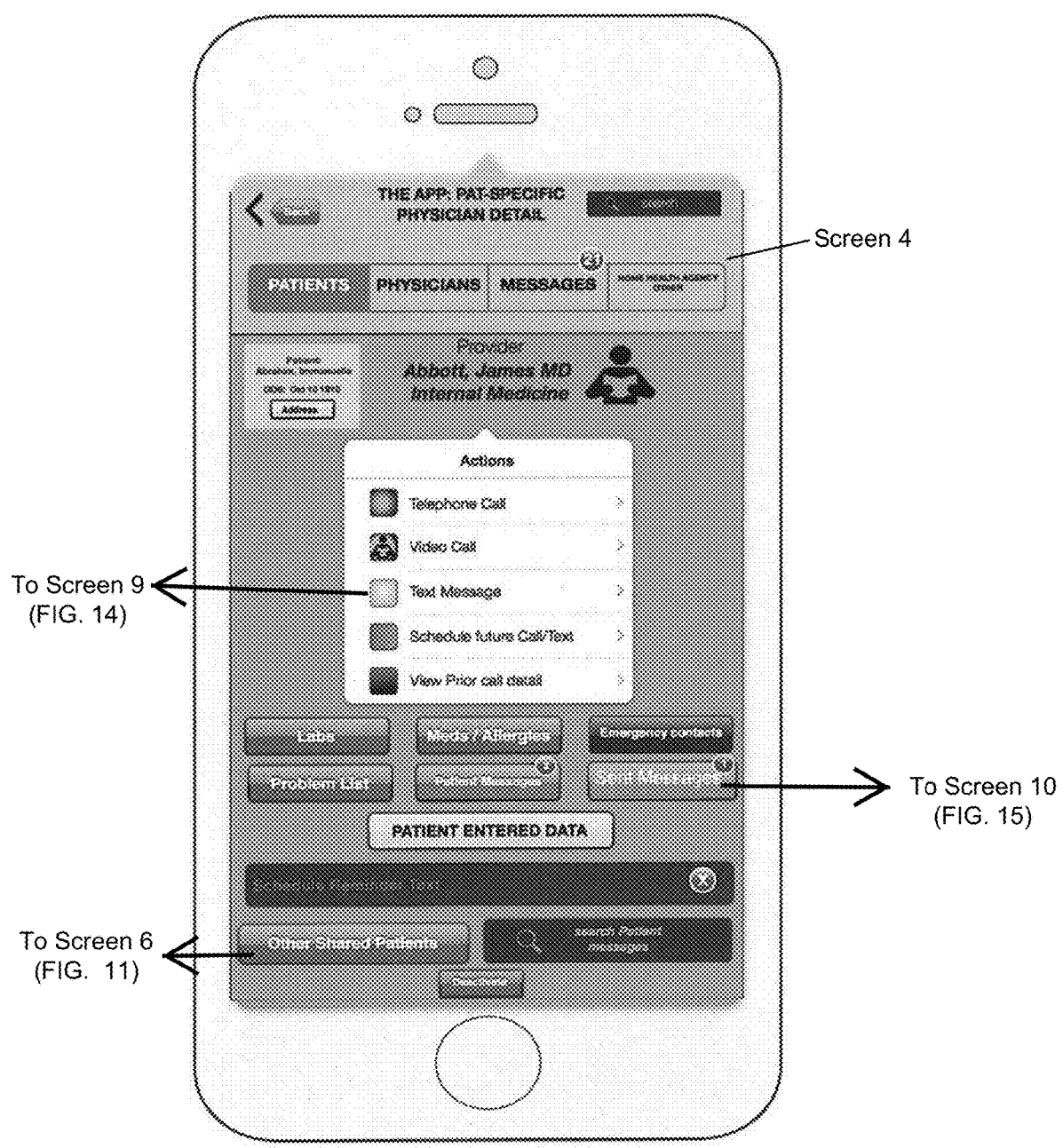
FIG. 9 is a patient specific physician details (physician owned) screen shot (Screen 4) providing various options to a physician regarding other physicians that are associated with the care of a particular patient.

FIG. 8 (Screen 3) provides details of the patient centered detail screen. In the example shown, a particular patient identified as Abrahim, Immanuelle is presented. In a window, the date of birth of this patient is presented and a button for obtaining the address of this patient. In the middle of the screen the MD or physician list is presented, that is, physicians which use the present invention and which provide healthcare to this particular patient. By selecting any of these healthcare providers, such as the identified James Abbott, detailed information concerning that healthcare provider is made available to the physician using this screen, leading to Screen 4 (FIG. 9). Other information beyond the PATIENTS, PHYSICIANS, MESSAGES, and HOME HEALTH AGENCY OTHER buttons are provided, such as LABS, PROBLEMS LIST, MEDS/ALLERGIES buttons. These lead to information populated by an HL-7 interface by regional or national labs, Surescripts, and EHR vendors as available. Selection of the buttons (regions) provides further information concerning the associated label. The LABS button provides any laboratory data which is available to this physician regarding this particular patient. Similarly, the MEDS/ALLERGIES button provides information regarding medications and allergies associated with this patient and the PROBLEM LIST button provides medical problems associated with this patient. An EMERGENCIES CONTACTS button allows the physician to access the patient's emergency contact information entered by the patient. In the example Screen 3, the PATIENT MESSAGES button shows that there are messages received about this patient with the numbered circle indicating how many messages and the SEND MESSAGES button indicates the number of messages sent about this patient to other providers. Furthermore, a reminder screen area is presented which provides information to the physician regarding this particular patient. For example, in the shown FIG. 8, a reminder is presented that this physician has scheduled a CT scan for a kidney scan and a discussion with radiology (regarding this patient) to be conducted on Jul. 28, 2014 and due by Aug. 15, 2014. The physician may also deactivate the link with the patient and archive their information by way of the DEACTIVATE button.

FIG. 9 (Screen 4) is a patient specific detail screen for another physician sharing the patient. Thus, actions, such as making telephone calls, video calls, text messages to schedule a future call or text message or to view prior call details are made available to the physician using the application with regard to the physician identified, in this case a Dr. James Abbott. This is with respect to a particular patient which is common (shared) between the physician using this application and the identified physician, namely, James Abbott. The common patient is the identified Abrahim, Immanuelle. The physician can also schedule future communications or view details for past communications. Reminder texts can also be scheduled. The physician can also access a list of all patient-specific messages to the other physician and view a list of other shared patients FIG. 10 (Screen 5) is a physician list screen which is selected by depressing the PHYSICIANS button from the main menu or other menus having that button. Detailed information can be accessed for each physician (Screen 8 (FIG. 13)) by selecting a physician from the list or a shared patient list (Screen 6 (FIG. 11)) can be accessed by selecting the number of patients next to a listed physician. It shows the number of patients that an identified physician has in common with the physician using the application (link 0) or physicians which are linked via another physician, but who themselves do not have a common patient with the physician using the applications (link 1).

For example, as shown in FIG. 3, Dr. D does not have any patients common with Dr. G, however, each has a patient common with Dr. A. (Dr. D has patient z common with Dr. A and Dr. G has patient v common with Dr. A). Thus, Drs. D and G would be a link 1 with respect to each other. A level 2 link would be a situation such as with regard to Dr. L with regard to patient t being common with Dr. G, where Dr. G has a patient v common with Dr. A, and Dr. D has a patient common with Dr. A (patient z).

Figure 10:
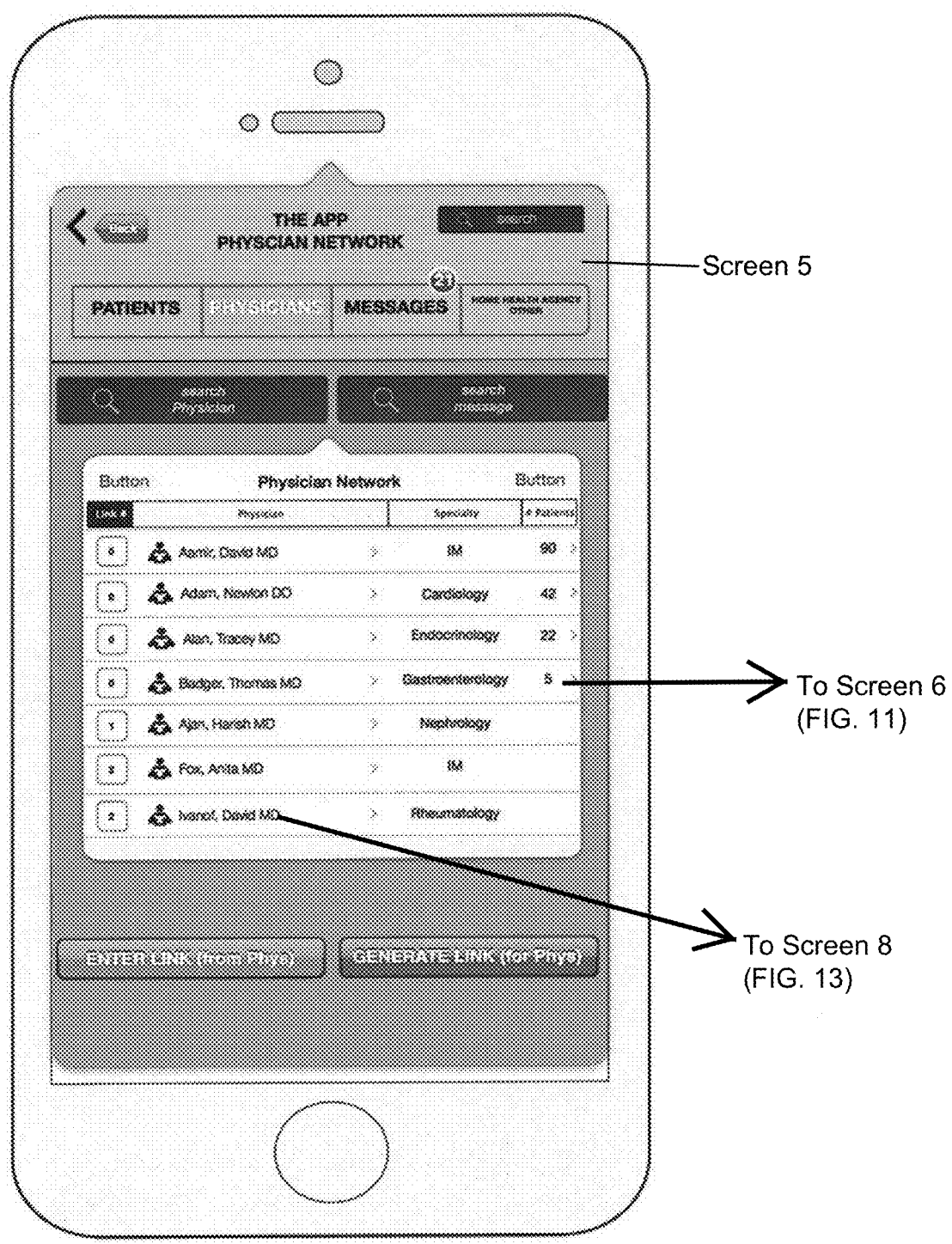
FIG. 10 is a physician network (physician owned) screen shot (Screen 5) indicating whether a particular physician is directly linked to the physician running the application and, if so, the degree of linking, that is whether the other physician provides care for the same patient as that of the physician running the application.

As shown in FIG. 10, the physician network provides buttons which allow for searching by alphabetical listing of physicians, by the order of linking between the physicians (link 0, 1, 2, etc.), as well as searching for a specialty associated with a particular physician. Furthermore, physicians with the highest number of common patients can also be searched by the (number # patients) button. New links can be entered for another physician in the network but not the user/physician's network (ENTER LINK (from Phys), and can be generated for other non-networked physicians (GENERATE LINK (for Phys)), to allow the non-network physicians to join the user/physicians network.

Figure 11:
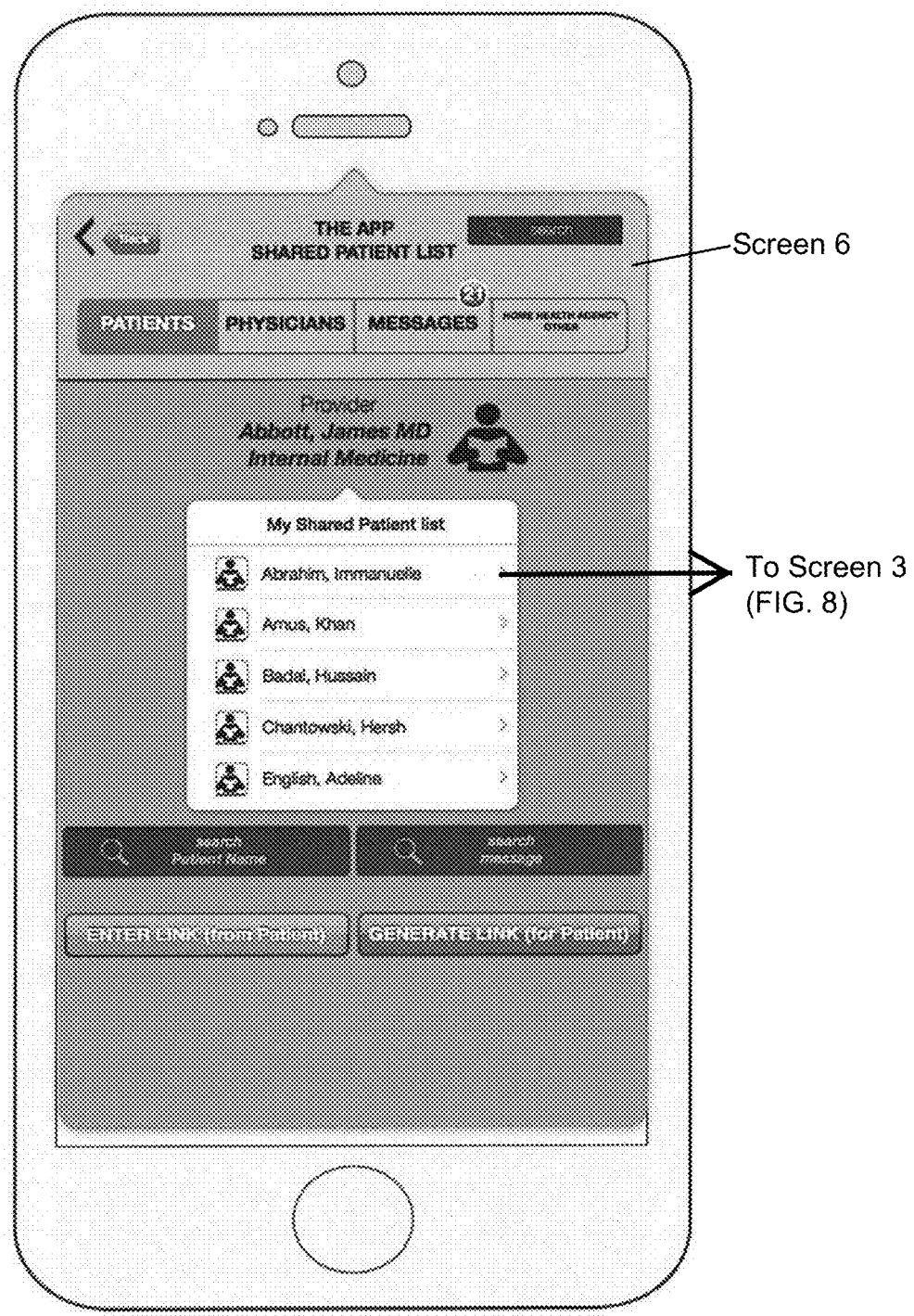
FIG. 11 is a shared patient list (physician owned) screen shot (Screen 6) showing all messages (physician owned).

FIG. 11 (Screen 6) is a shared patient list screen which can be selected from the physician detail screens (Screen 8 (FIG. 13) or Screen 4 (FIG. 9)). The shared patient list screen provides information regarding patients which are shared or common between the physician using the application and another physician who also provides care to that particular patient. Thus, it can be quickly determined through use of the present invention what other patients are shared between, for example, Dr. A and Dr. E when initially only one patient (for example, patient y) is initially known between Drs. A and E. By knowing what additional patients are shared between, for example, Drs. A and E allows those doctors to become more efficient in their delivery of healthcare to these other shared patients since communications can be made between Drs. A and E not only for the initial patient which was determined as shared between them (for example, patient y), but also any other patients which are then determined to be shared between Drs. A and E, as shown in FIG. 3.

Figure 12:
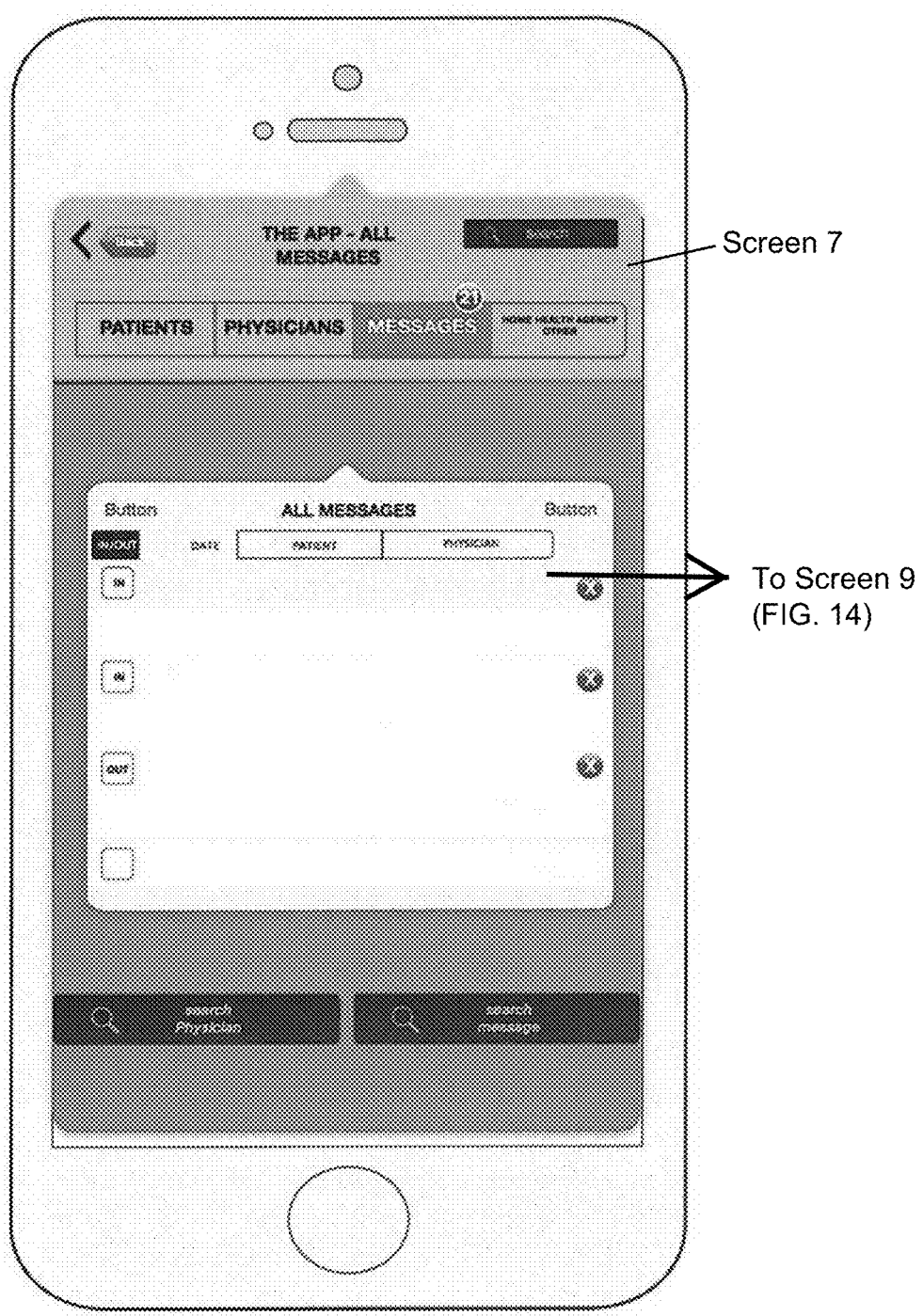
FIG. 12 is a screen shot (Screen 7) showing all messages (physician owned).

FIG. 12 shows the Messages screen (Screen 7), which can be opened by selecting the MESSAGES button from the top menu bar. The listing of messages indicates whether it is in the Inbox or Outbox and the related patient and/or physician. Selecting a particular message leads to the patient-specific provider message, shown in Screen 9 (FIG. 14).

Figure 13:
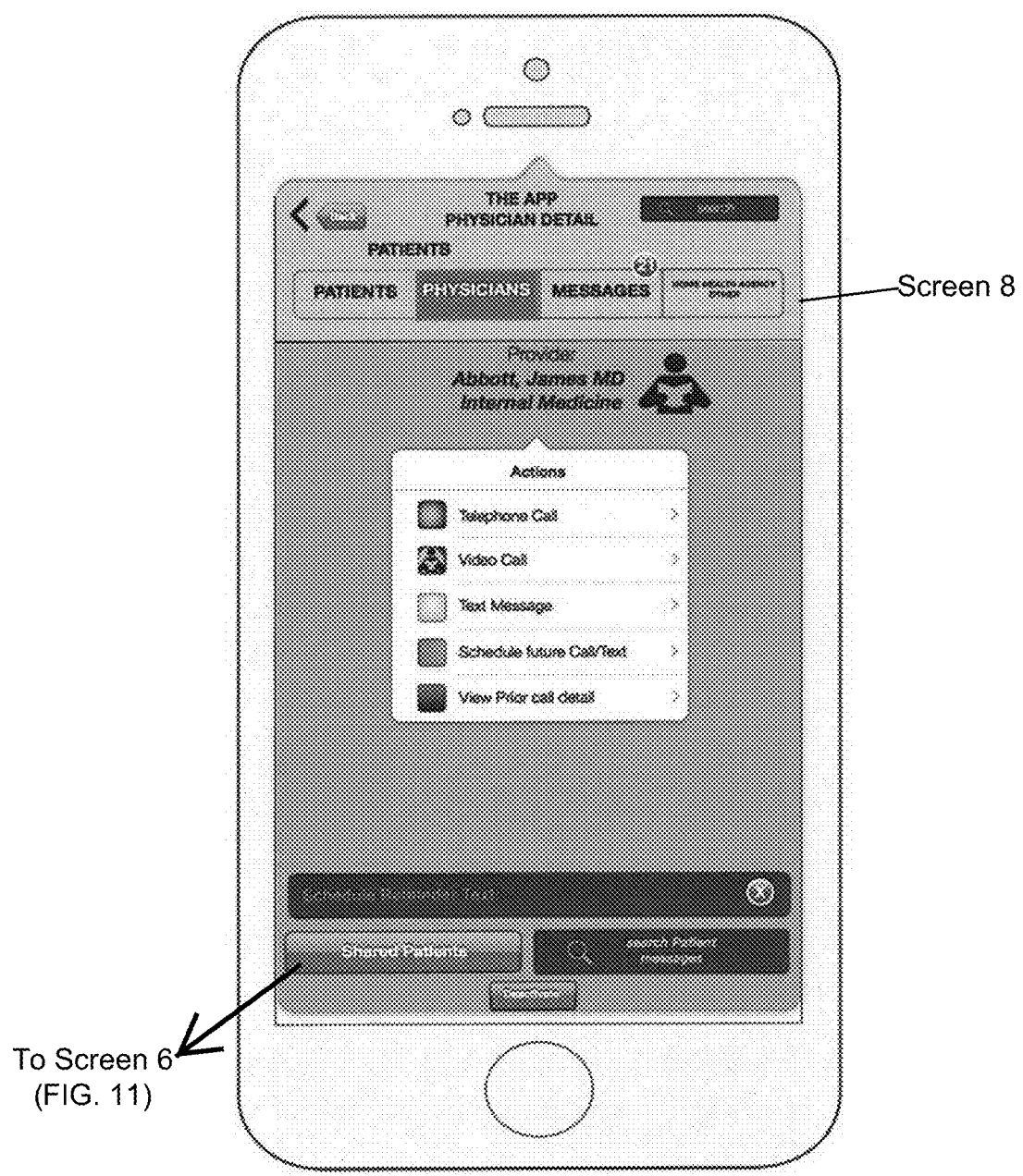
FIG. 13 is a screen shot (Screen 8) showing physician details for non-patient linked physician (physician owned).

FIG. 13 (Screen 8) is the physician detail screen which provides detailed information regarding a selected physician from Screen 3 (FIG. 8). Thus, actions, such as making telephone calls, video calls, text messages to schedule a future call or text message or to view prior call details are made available to the physician using the application with regard to the physician identified, in this case a Dr. James Abbott. A reminder screen is also presented on this screen which allows for reminder texts to be displayed and scheduled to the selected physician using the application. The OTHER SHARED PATIENTS button allows the physician using the application to determine not only the current patient that is common between the physician using the application and the other physician (James Abbott), but also other patients which are common between these two physicians. A DEACTIVATE button is also shown which allows the application to be deactivated, with respect to links of a particular patient and to archive information in compliance with HIPAA.

Figure 14:
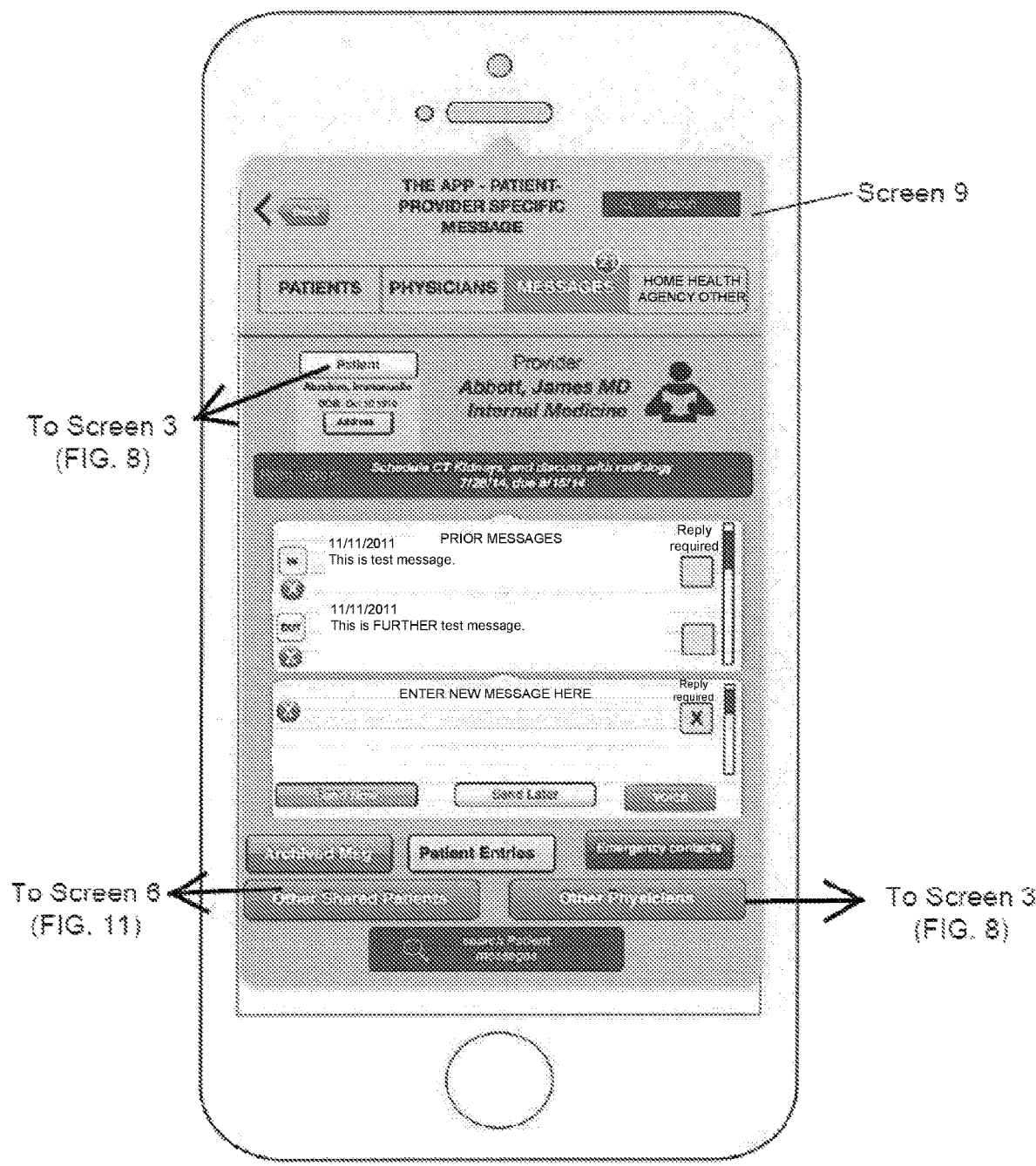
FIG. 14 is a patient specific-provider message screen shot (Screen 9) (physician owned).

FIG. 14 (Screen 9) shows the patient specific-provider message screen (physician-owned). This screen shows prior messages with another particular physician and allows for the entering of new messages to send by text or voice. Archived or deleted messages can also be accessed, along with other physicians linked with the particular patient and other patients linked with the other physician.

Figure 15:
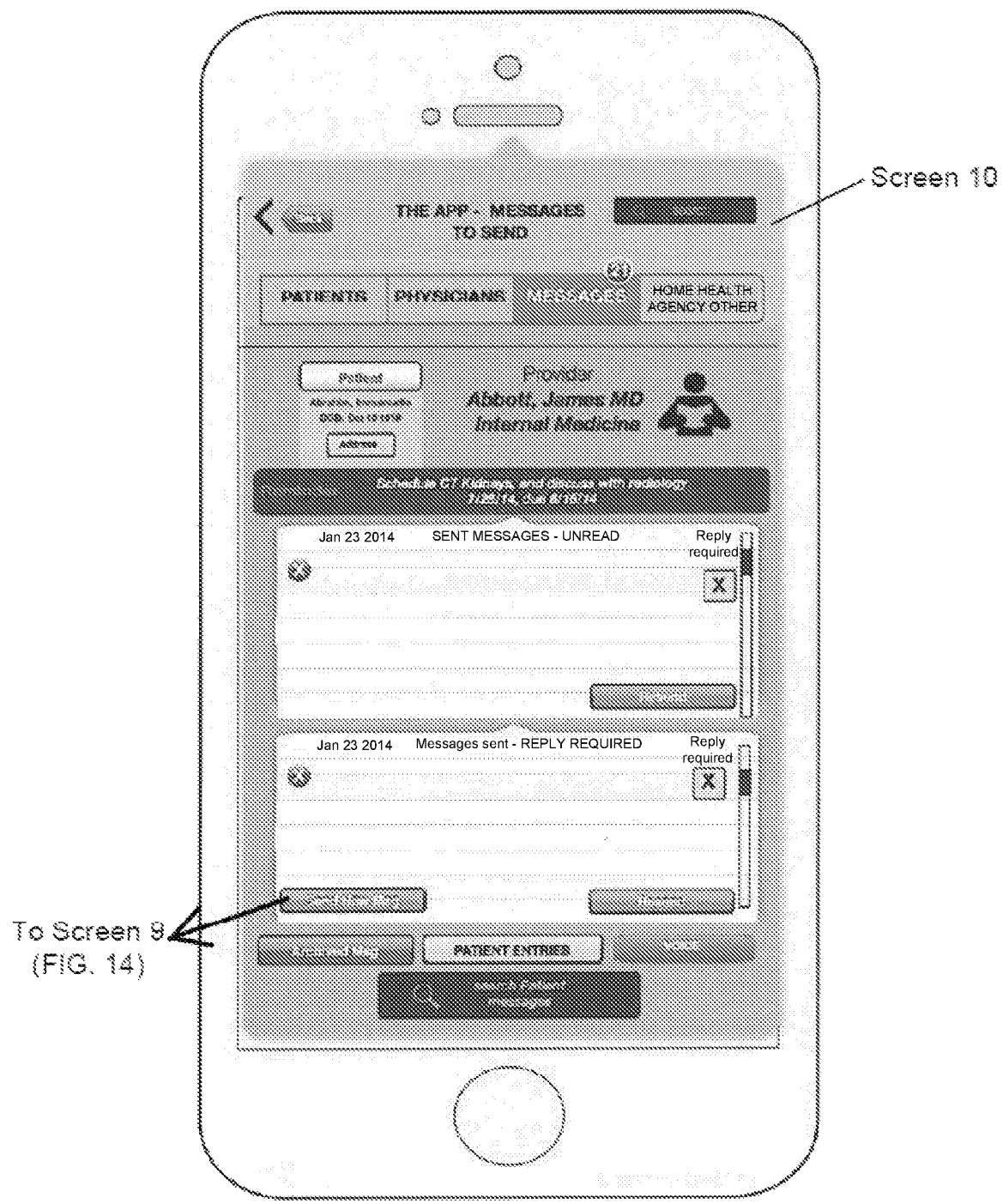
FIG. 15 is a patient specific provider messages to send screen shot (Screen 10).

FIG. 15 (Screen 10) shows the patient specific-provider messages to send screen, which can be accessed from Screen 4 (FIG. 9), for example. Sent messages that are unread and sent messages that have not been replied to (where a "Reply was Needed" identification was attached) are displayed and can be resent. Telephone calls to the physician can also be initiated by the VOICE button.

Figure 16:
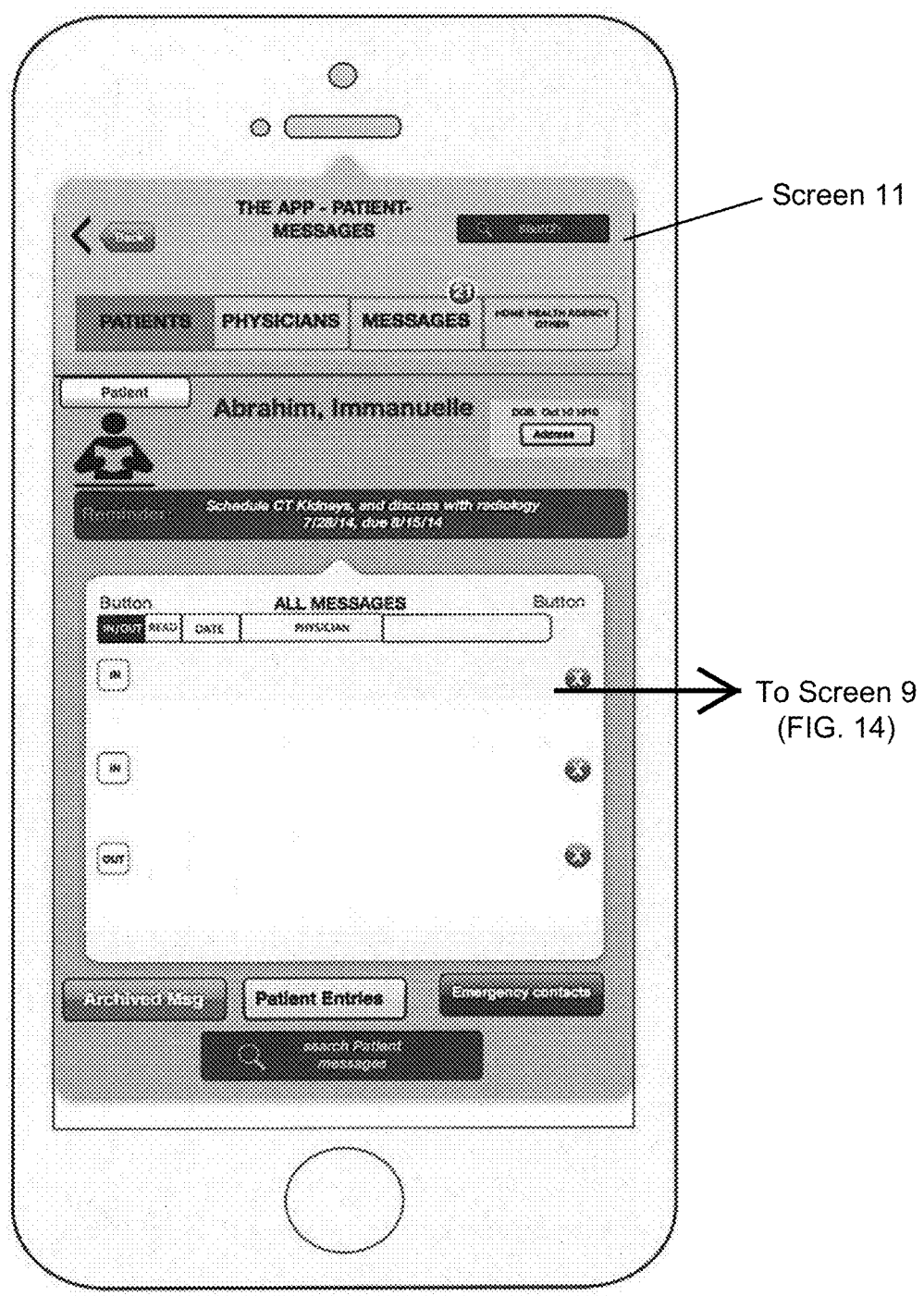
FIG. 16 is a patient specific message screen shot (Screen 11) for messages from all physicians (physician owned).

FIG. 16 (Screen 11) shows the patient specific messages from all physicians (physician-owned) for a particular patient. This includes a list of messages and whether the message is in the INBOX or OUTBOX, whether the message has been read, and the physician related to the message.

Figure 17:
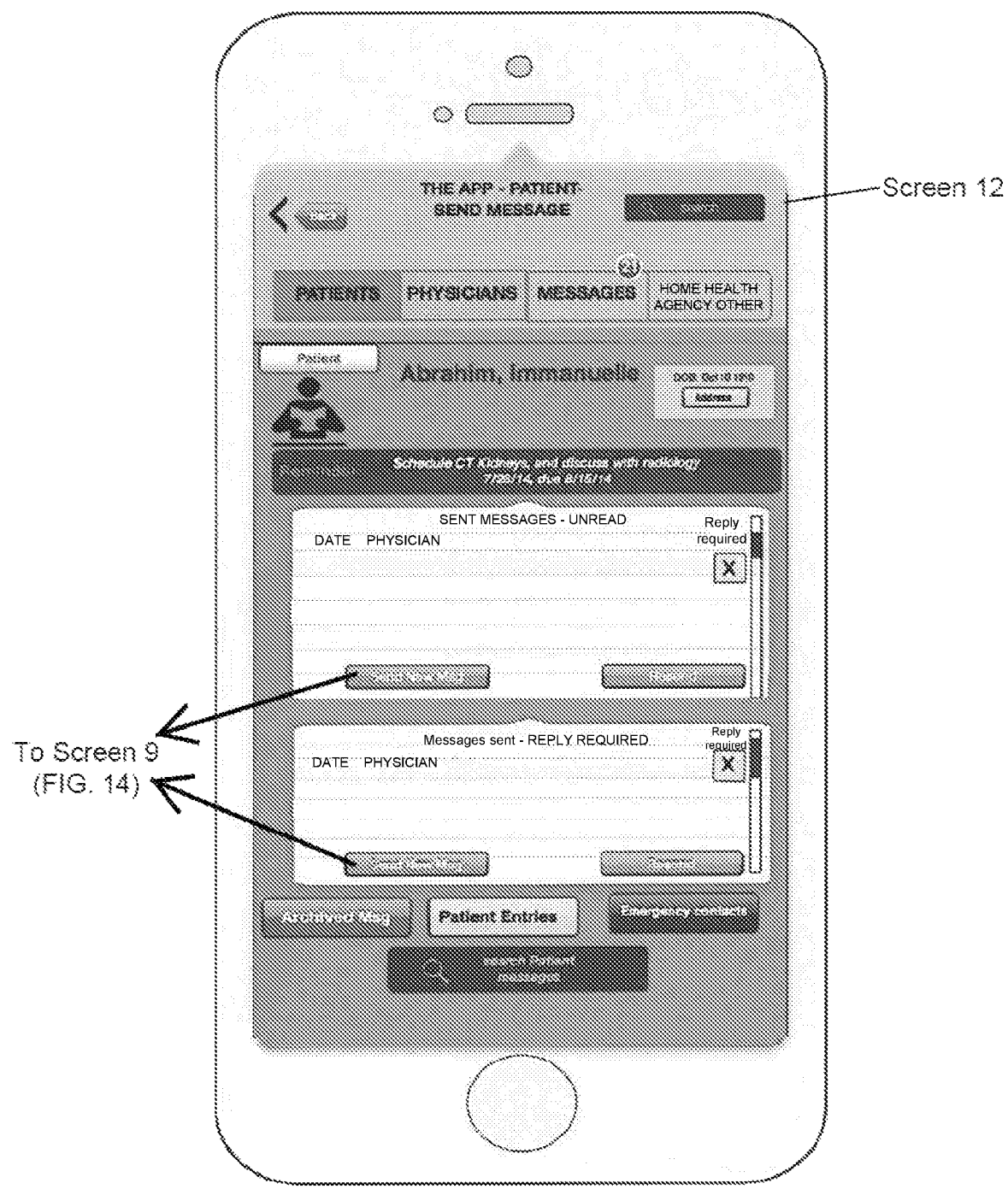
FIG. 17 is a screen shot showing patient-specific messages to send for all physicians (physician-owned).

FIG. 17 (Screen 12) shows the patient specific messages to send for all physicians (physician-owned) for a particular patient. Sent messages that are unread and sent messages that have not been replied to (where a "Reply was Needed" identification was attached) are displayed and can be resent, and new messages can be sent.

FIGS. 18-22 show various screens that can be accessed by a patient in accordance with the present invention.

Figure 18:
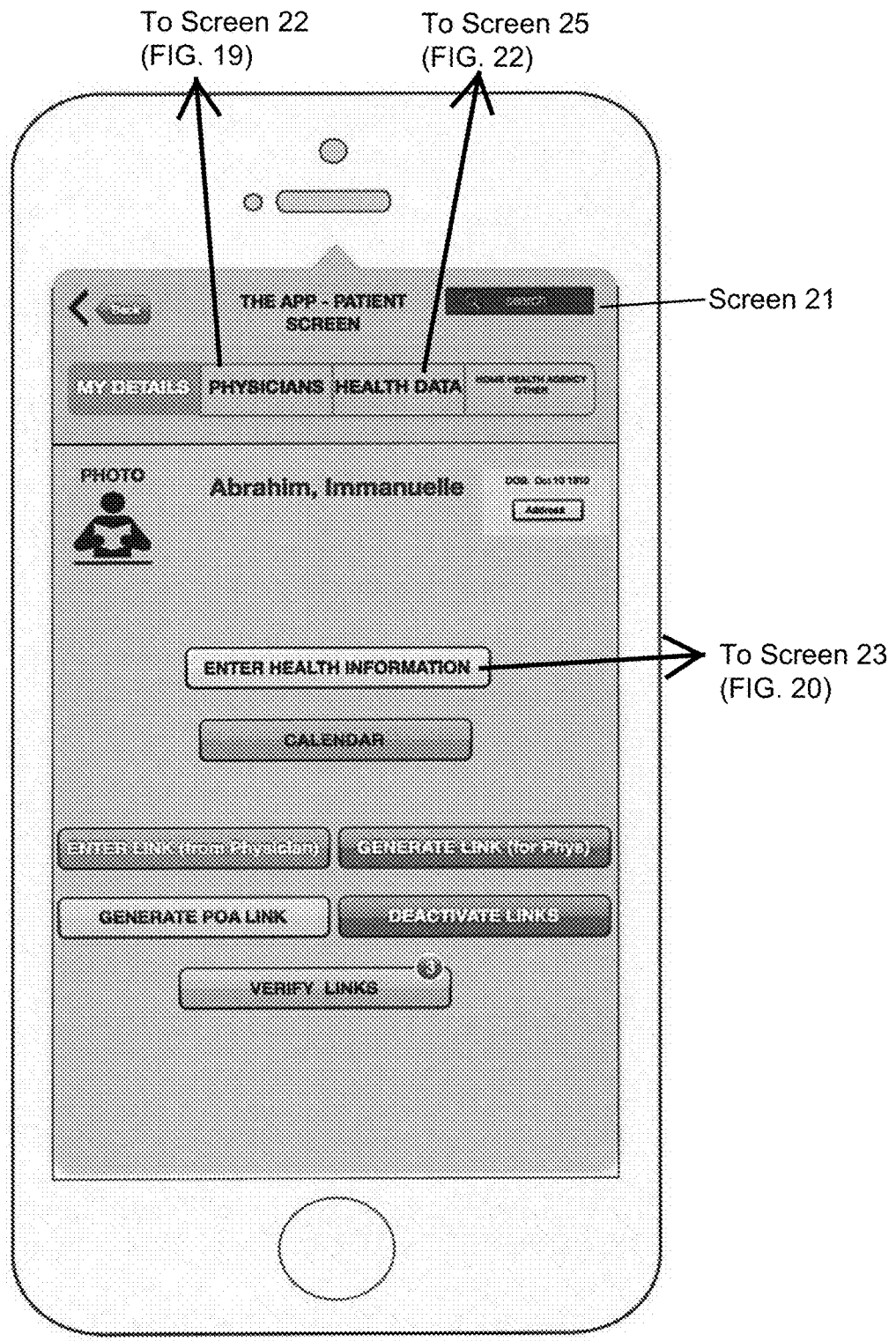
FIG. 18 is a main patient screen shot (Screen 21).

FIG. 18 (Screen 21) shows the main patient screen or home screen, that is, the information available to a patient using an application according to the present invention. In the example show, the patient is Immanuelle Abrahim. The user's date of birth is shown and a photo can be included if desired. A calendar is provided for the user to enter and view appointments. The user can enter their health information, such as blood pressures, weights, and other information manually, or if available in accessible database, the information can be imported. New links can be entered for a physician registered in the network but not yet on the user/patient's network (ENTER LINK (from Physician)), and can be generated for other non-networked physicians (GENERATE LINK (for Phys)), to allow the non-network physicians to join the patient's network. The user can also generate a link for a significant other to have partial access to the user's network (GENERATE POA LINK), in the event that the other individual needs access to certain information. The physician may verify link requests in progress from other physicians with the VERIFY LINKS button and deactivate links that are no longer active, such as for physicians who have moved out of the area, via a DEACTIVATE LINKS button.

Figure 19:
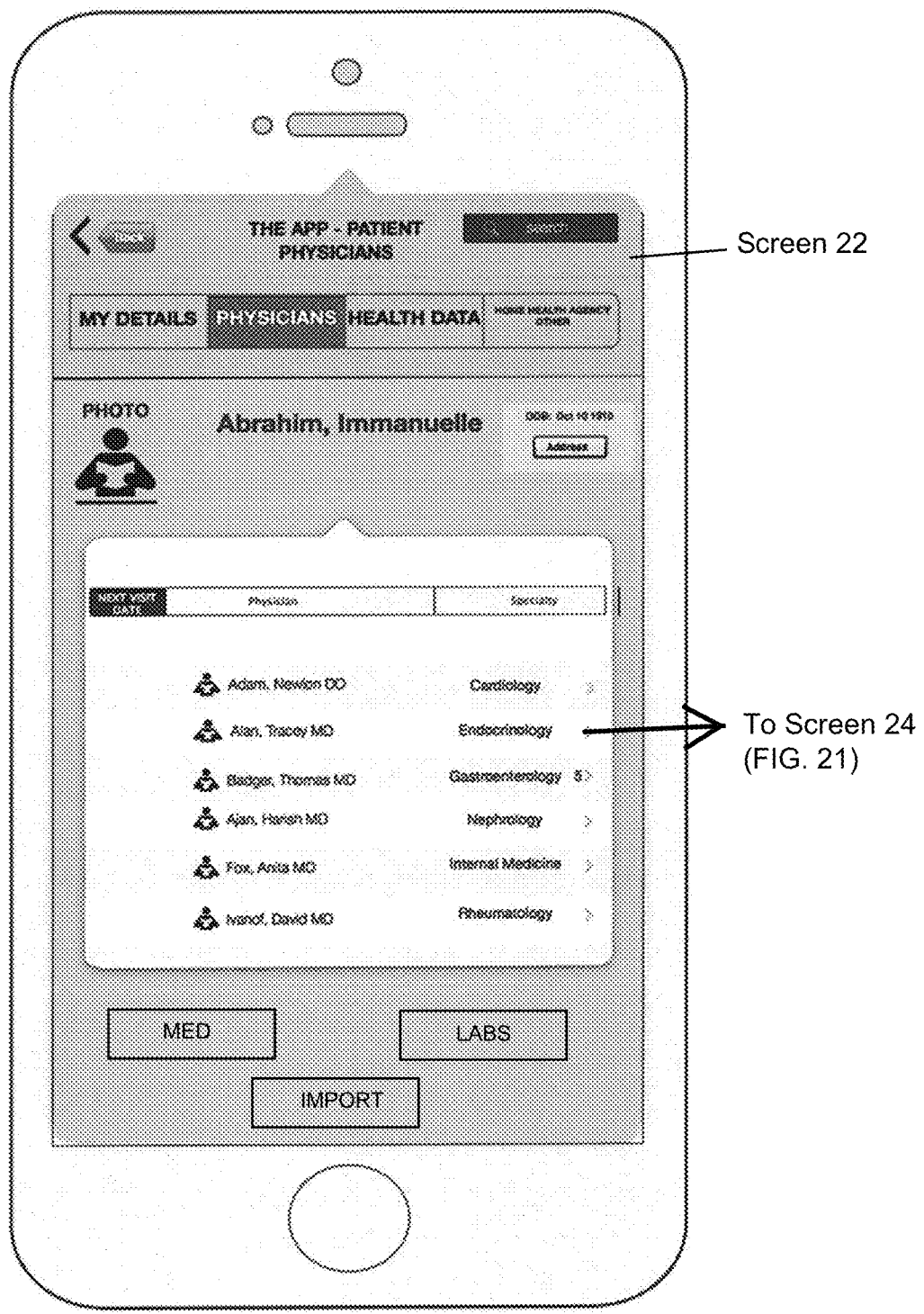
FIG. 19 is a patient physician list (Screen 22) (patient-owned).

FIG. 19 (Screen 22) shows the patient's physician list, that is, physicians providing healthcare to this particular patient which are included in the patient's network in the system of the invention. The user can access further information relating to each physician (Screen 24 (FIG. 21)) by selecting a physician from the list.

Figure 20:
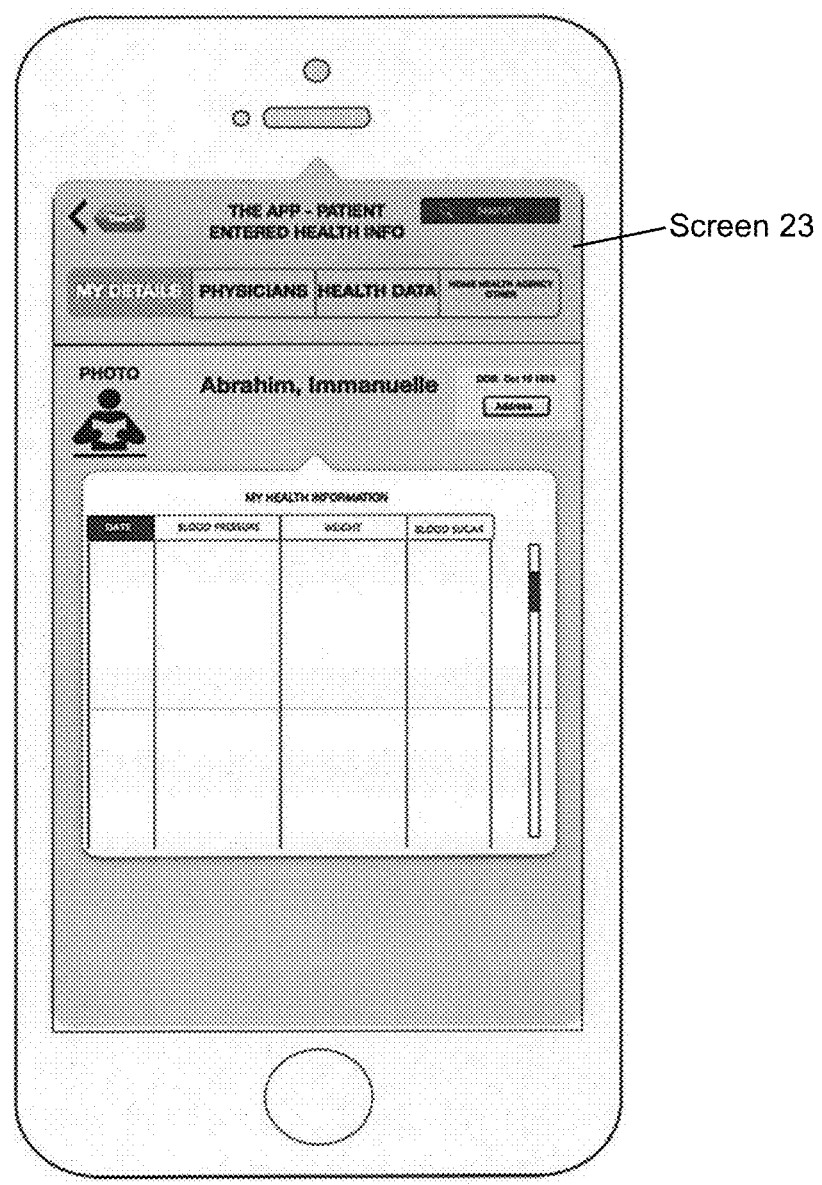
FIG. 20 is a screen shot (Screen 20) for patient entered health information.

FIG. 20 (Screen 23) is a patient entered health information screen which allows the patient to enter healthcare data which can then be made available to an attending physician of that patient. It is also possible that data, if available in an accessible database, can be imported into the system from the database by the user.

Figure 21:
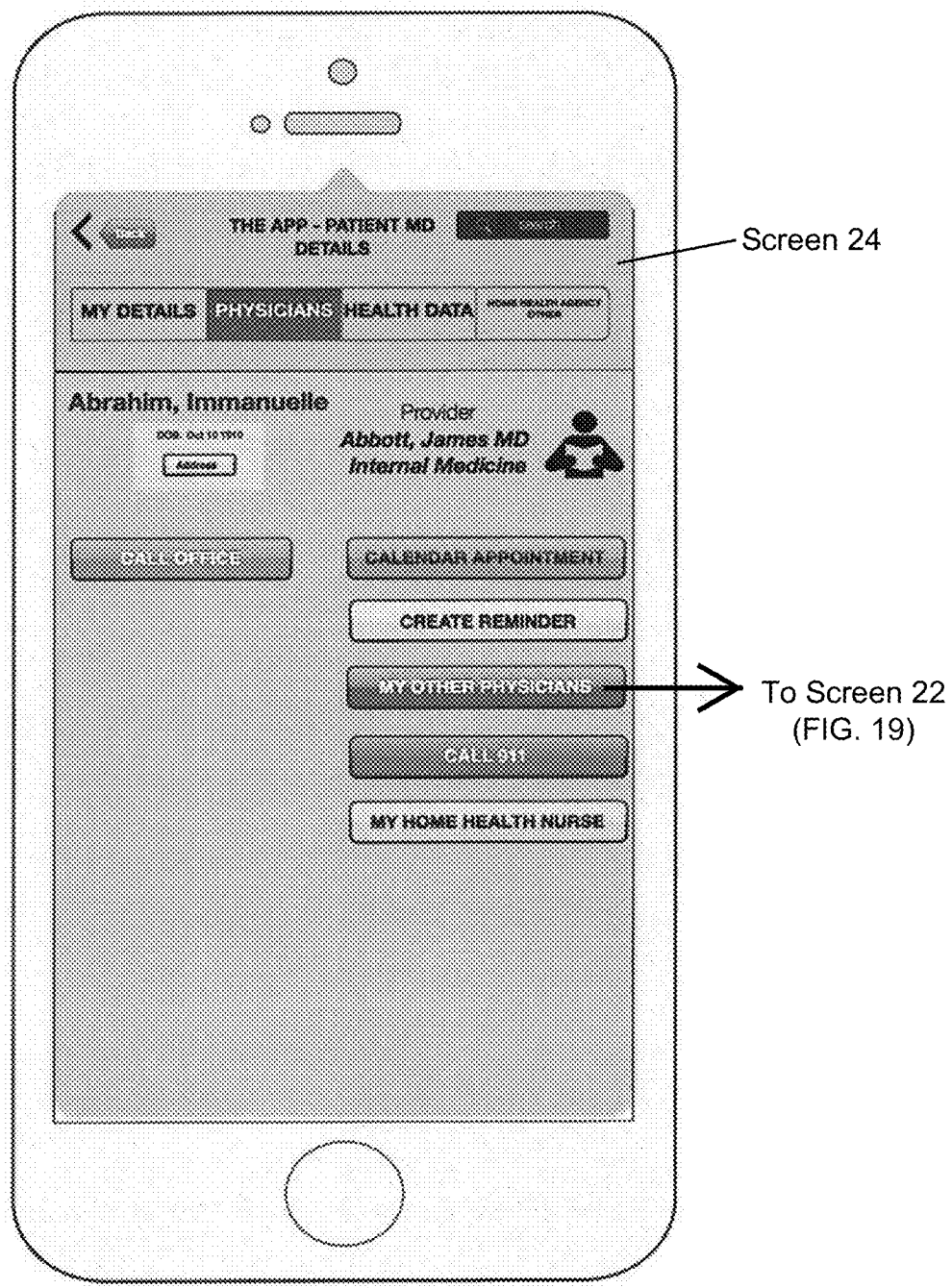
FIG. 21 is a screen shot (Screen 24) of a patient physician details (patient-owned).

FIG. 21 (Screen 24) is a patient physician detail screen (patient-owned) which provides the patient with specific information regarding a physician providing care to that patient. The user can contact the physician by the CALL OFFICE button, can enter an appointment into the user's calendar by selecting the CALENDAR APPOINTMENT button, and can generate reminders using the CREATE REMINDER BUTTON. The user can also access the list of all of his or her physicians through the MY OTHER PHYSICIANS button or connect to other health professionals through the MY HOME HEALTH NURSE button.

Figure 22:
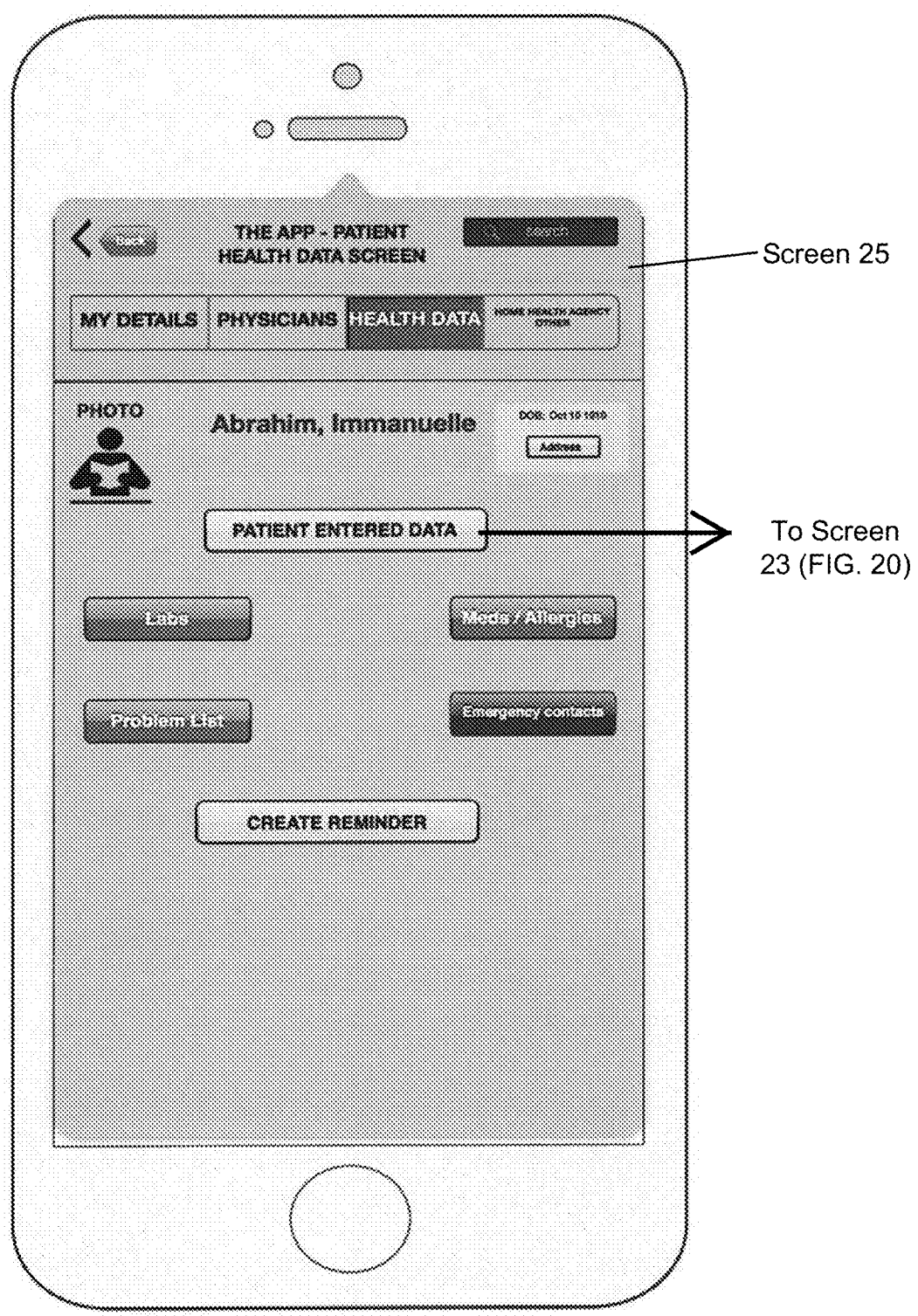
FIG. 22 is a screen shot (Screen 25) for a patient's healthcare data screen-interfaced as available (patient-owned).
Figure 23:
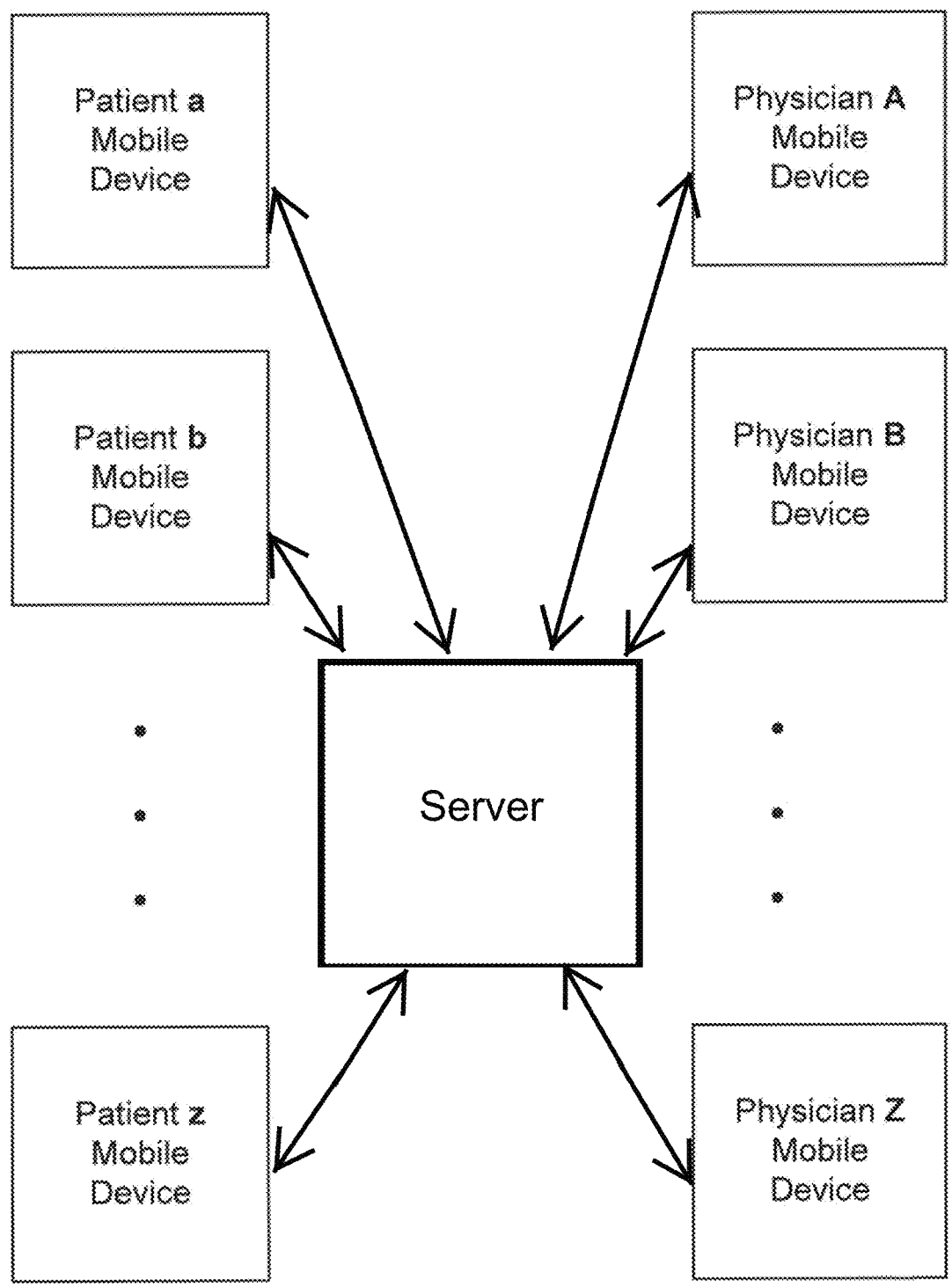
FIG. 23 is a general block diagram showing various mobile devices operating applications according to the present invention for both patients and for physicians.

FIG. 22 (Screen 25) presents a patient health data screen with interfaces as shown. Thus, the patient can obtain information regarding laboratory reports, medications used, etc. by selecting various buttons shown. This information can be populated by an HL-7 interface by regional or national labs, Surescripts, and EHR vendors as available. The user can also add or edit their emergency contacts and access their medical data (Screen 23 (FIG. 20)) to edit or add data FIG. 23 is an overall block diagram showing various mobile devices which are implementing either the patient application or the physician application as described above. Each mobile device includes a processor and a memory including computer program code for execution, where the memory and computer program code are configured to, with the processor, cause the overall system to perform the actions recited above either with respect to the physician-owned application or the patient-owned application. Each mobile device further includes a user interface, a display, a transmitter and a receiver. It is well-known in the art that although mobile devices are shown, the physician based application and/or the patient based application could also be implemented on any other computer oriented hardware, such as a tablet, laptop or desktop computer as long as networking capability is available. The mobile device may include wireless communication capabilities for communicating, such as via a wireless cellular network to other wireless devices operating applications according to the present invention.

In FIG. 23, a plurality of physicians from A-Z and a plurality of patients from a-z are shown. Any number of patients may be associated with any particular physician(s) and any number of physicians can be linked to a particular patient(s). FIG. 23 is thus illustrative of a typical implementation of the hardware associated with the present invention.

According to the invention and shown in FIG. 23, a remote and secure server is also provided for storing, accessing and transmitting the relevant patient data to the authorized users of the application. In certain embodiments of the invention, the server can be cloud-based. The server according to the invention comprises a memory, a processor, a transmitter and a receiver, as would be understood by a person of ordinary skill in the art, and is configured to communicate with the patient and physician devices. The patient's health data can be stored on the server, from which the application can make secure RESTful API calls to post and get the data. Modern web technologies can be utilized, such as Ruby on Rails or Django, which can interact with a database such as MySQL or MongoDB, to provide the data to users.

An alternative embodiment of the present invention is shown in FIGS. 24A-25G, which shows flow charts diagramming the operation of the invention from the physician side (FIGS. 24A-24R) and the patient side (FIGS. 25A-25G).

Figure 24A:
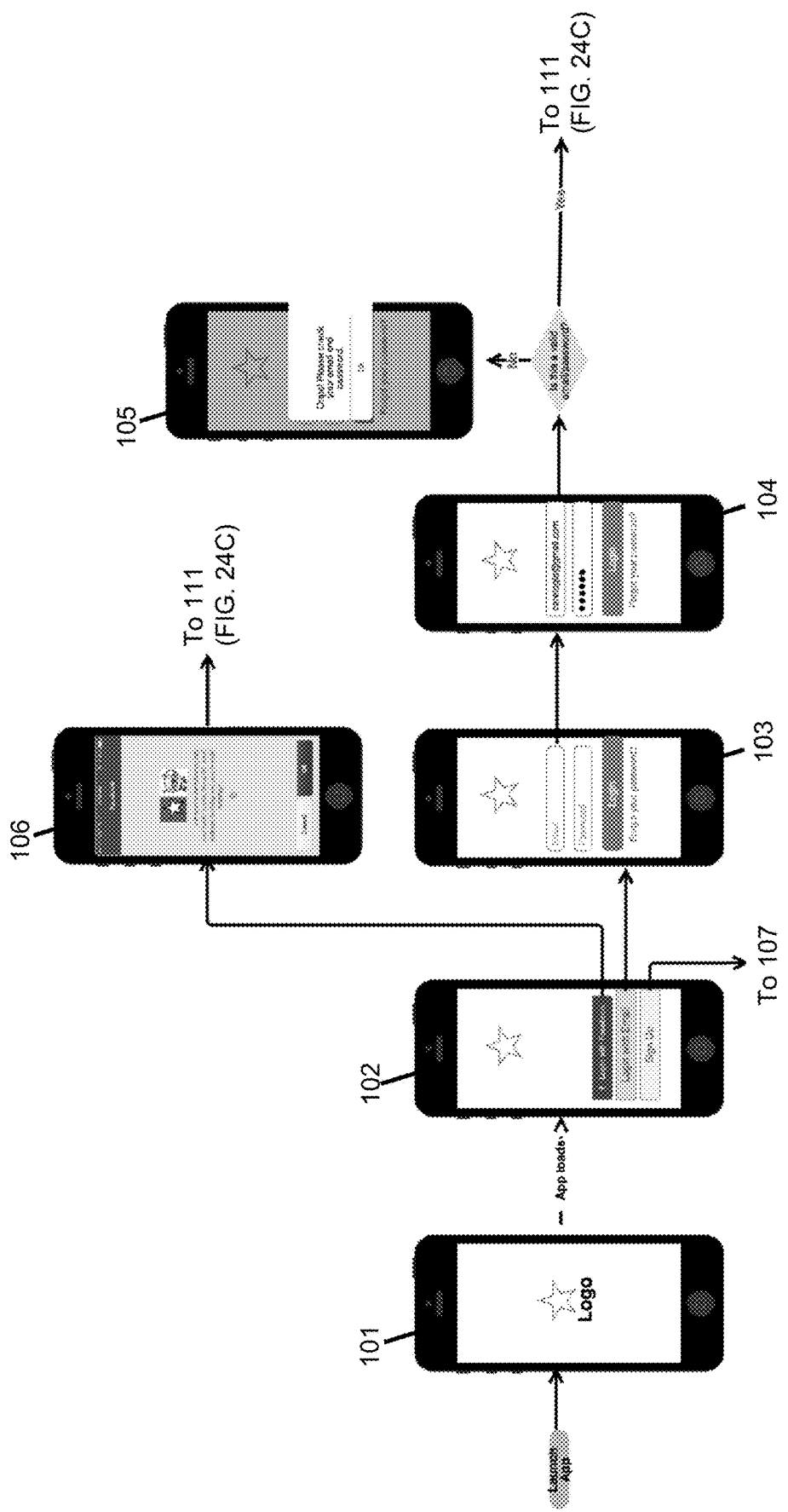
FIGS. 24A-24R show a flow chart showing operation of a second embodiment of the present invention and, in particular, various application screens that are seen on the physician-side implementation of the present invention.
Figure 24B:
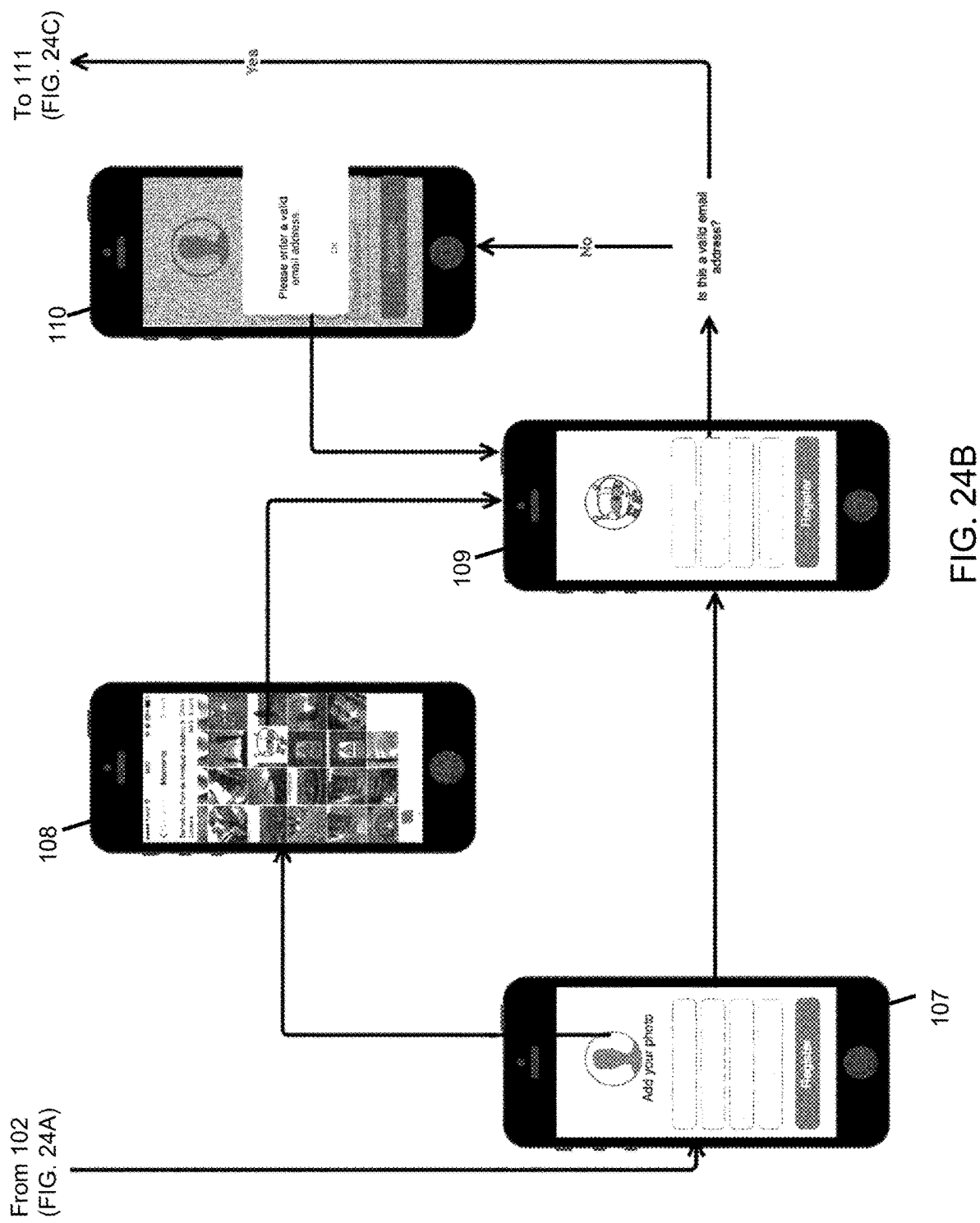

In FIG. 24A, Screens 101-106 show the launching of the system from the physician side and an example of a manner for accessing the system. If a user/physician is accessing the system for the first time, the user may establish an account with a user name and password for accessing the system, as shown in Screens 107-110 in FIG. 24B. If an invalid email address or password is provided, then the user can be directed to attempt a further log-in, set up a new account, or provide verifying information to change the user's password or confirm email address. The screens for establishing an account further include the ability for the user to add personal information to accompany their account.

Figure 24C:
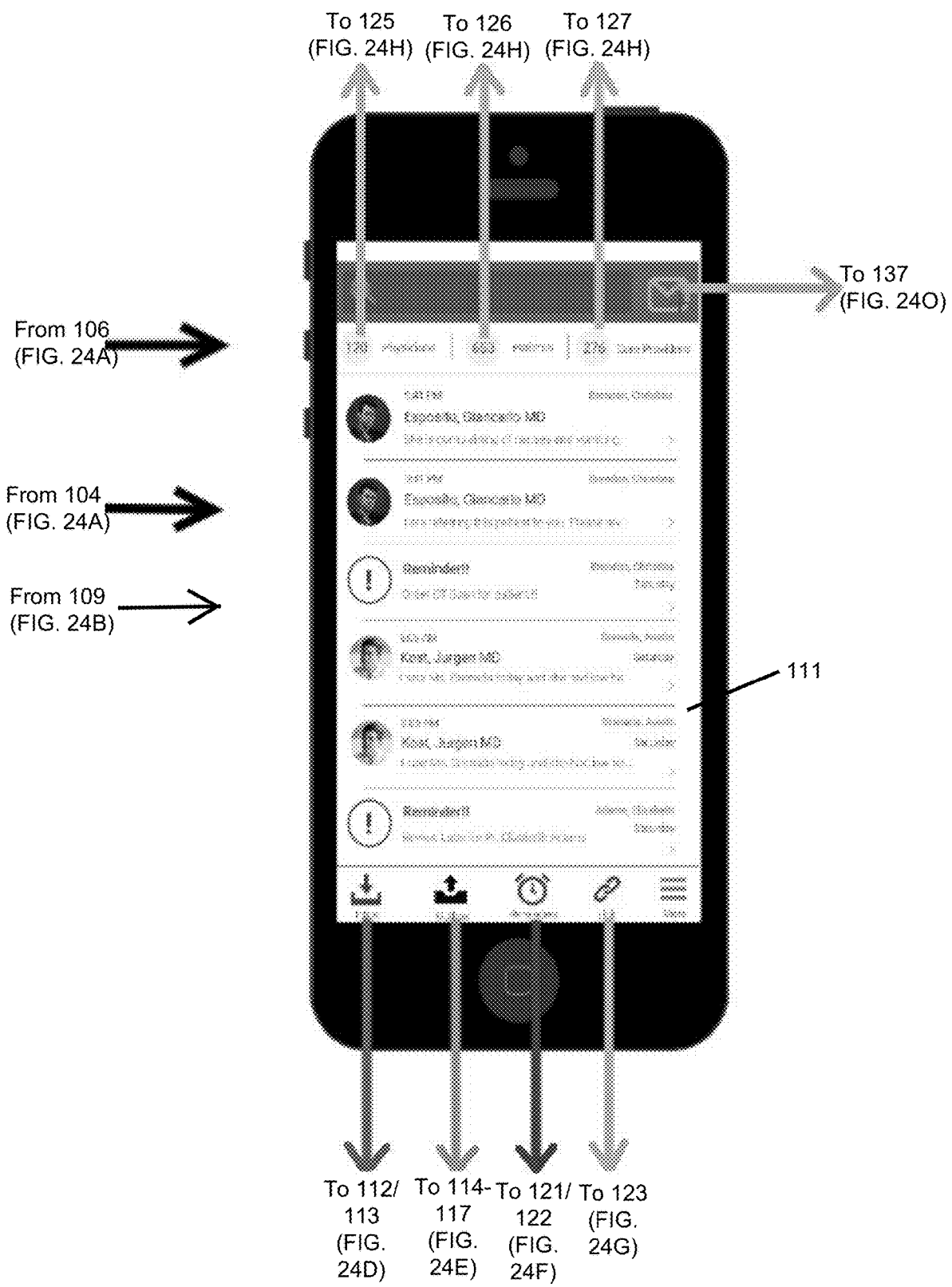

Screen 111, shown in FIG. 24C, depicts a home screen according to the second embodiment of the invention, with aggregated notifications and messages for the user. From this screen, the user can access his or her network of other physicians (Screen 125, FIG. 24H), patients (Screen 126, FIG. 24H) or other care providers (Screen 127, FIG. 24H). The user can also access from the home screen the ability to create new messages (Screen 137, FIG. 24O), the user's inbox (Screens 112 and 113, FIG. 24D), the user's outbox (Screens 114-117, FIG. 24E), the user's reminders (Screens 121 and 122, FIG. 24F) and the user's links (Screen 123, FIG. 24G).

Figure 24D:
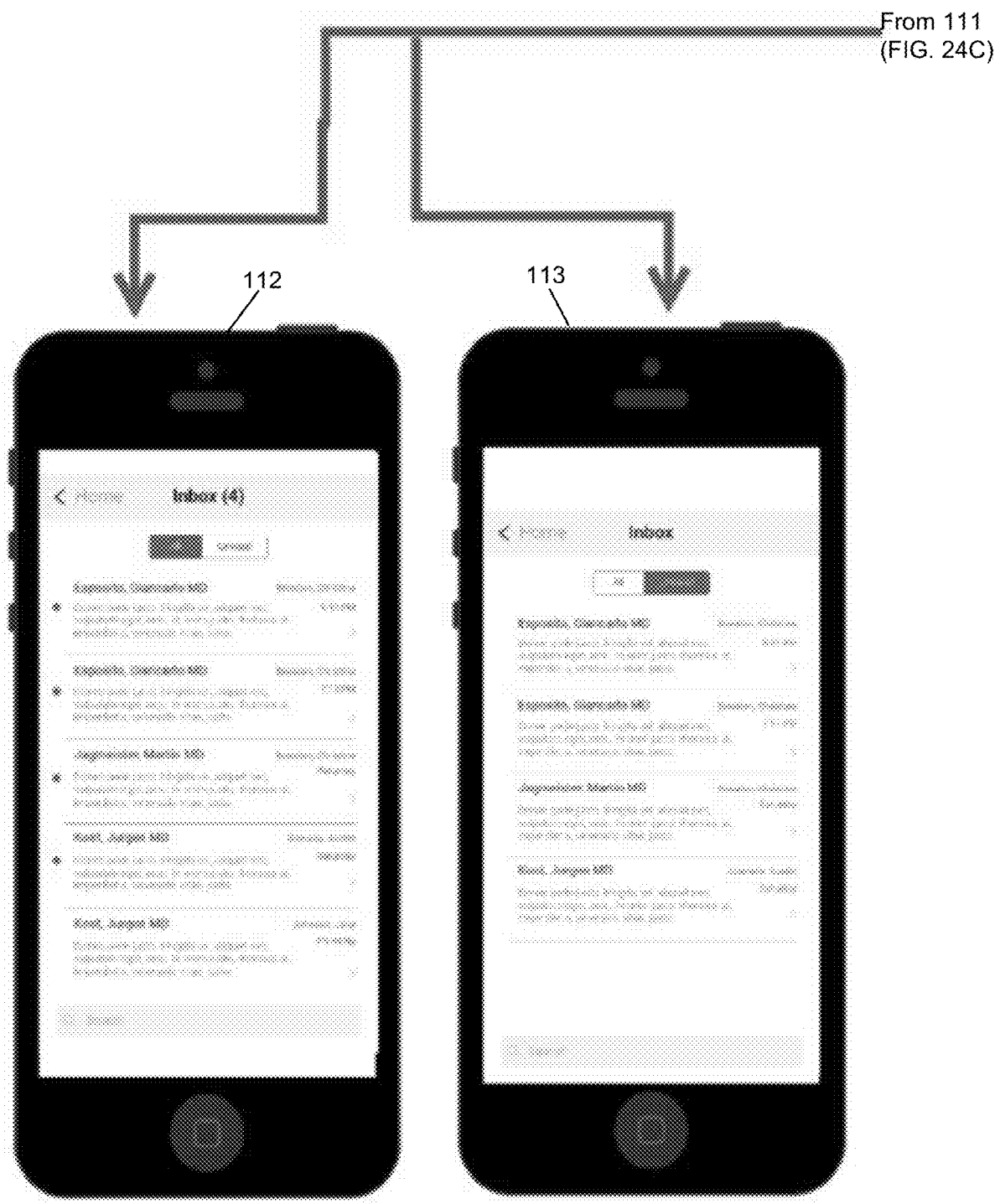
Figure 24E:
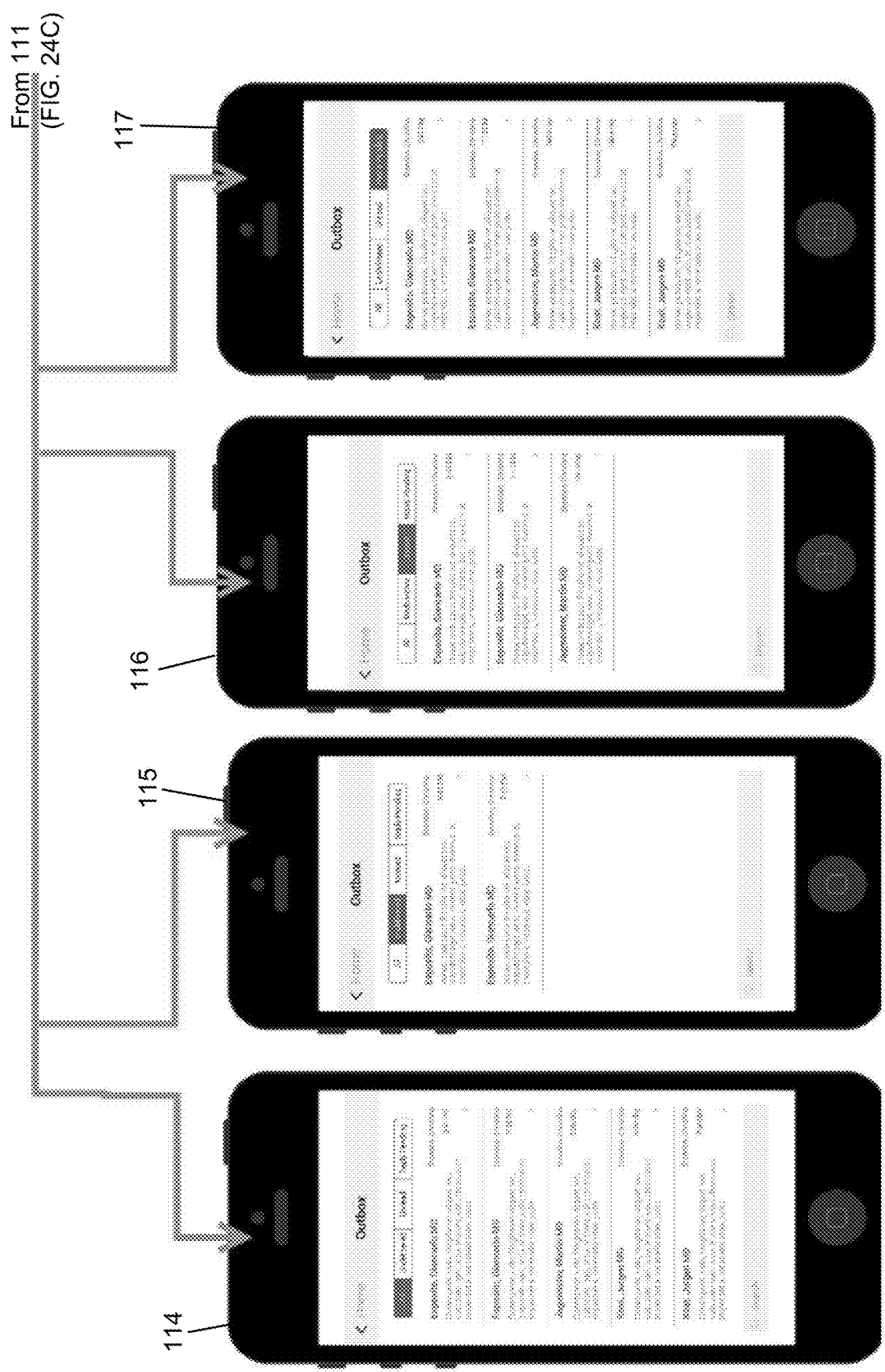
Figure 24F:
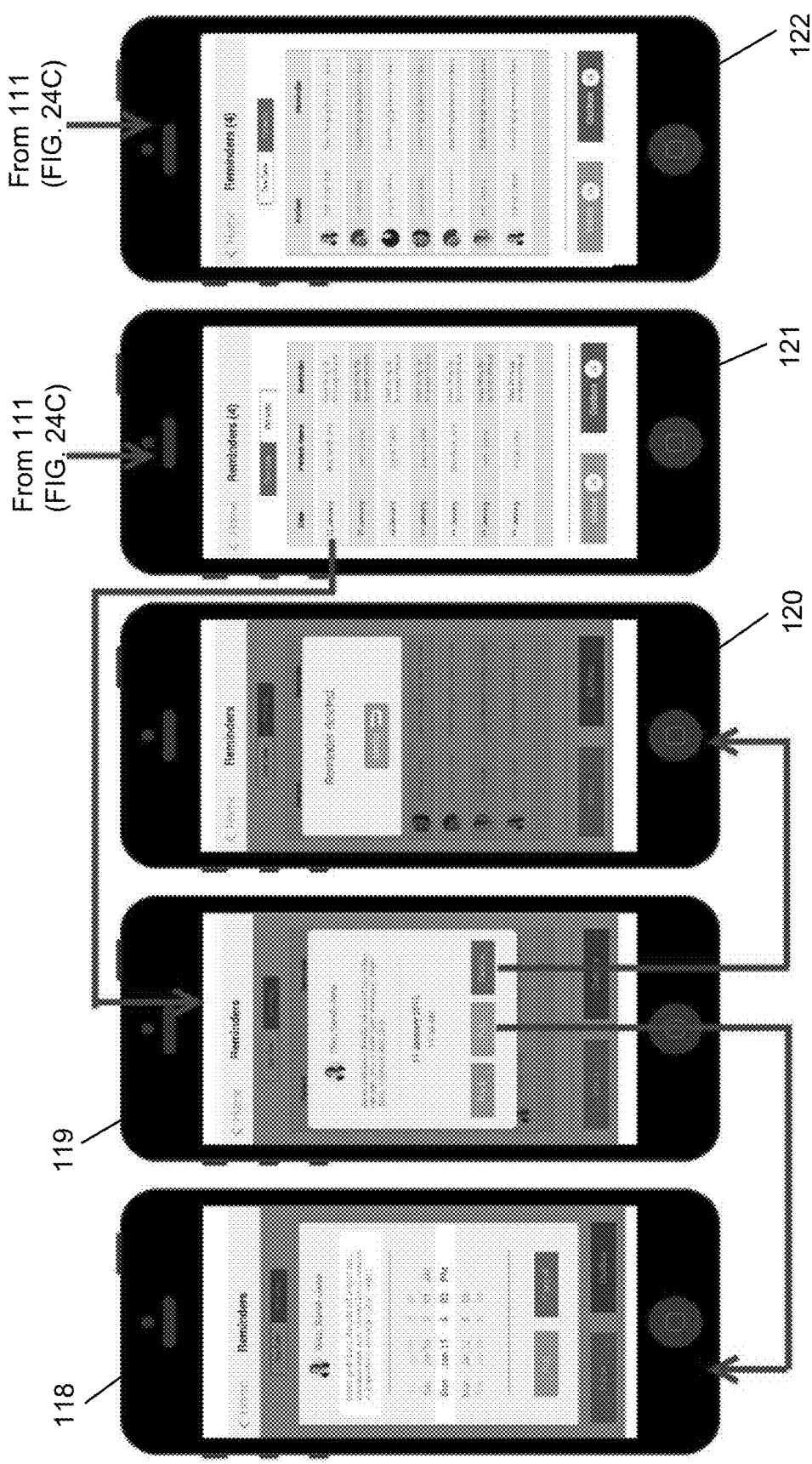

The user's inbox, shown in FIG. 24D, may include viewing options, for example, to show all messages (Screen 112) or only unread messages (Screen 113). The user's outbox, shown in FIG. 24E, may include viewing options, for example, to show all messages (Screen 114), undelivered messages (Screen 115), unread messages (Screen 116) or messages with a reply pending (Screen 117). The user's reminders in the system can also be accessed (FIG. 24F) and organized, for example, by the date of the event (Screen 121) or by the patient associated with the event (Screen 122). By selecting a particular event (Screen 119), the user can view detailed information the subject of the reminder and can edit (Screen 118) or delete (Screen 120) the reminder.

Figure 24G:
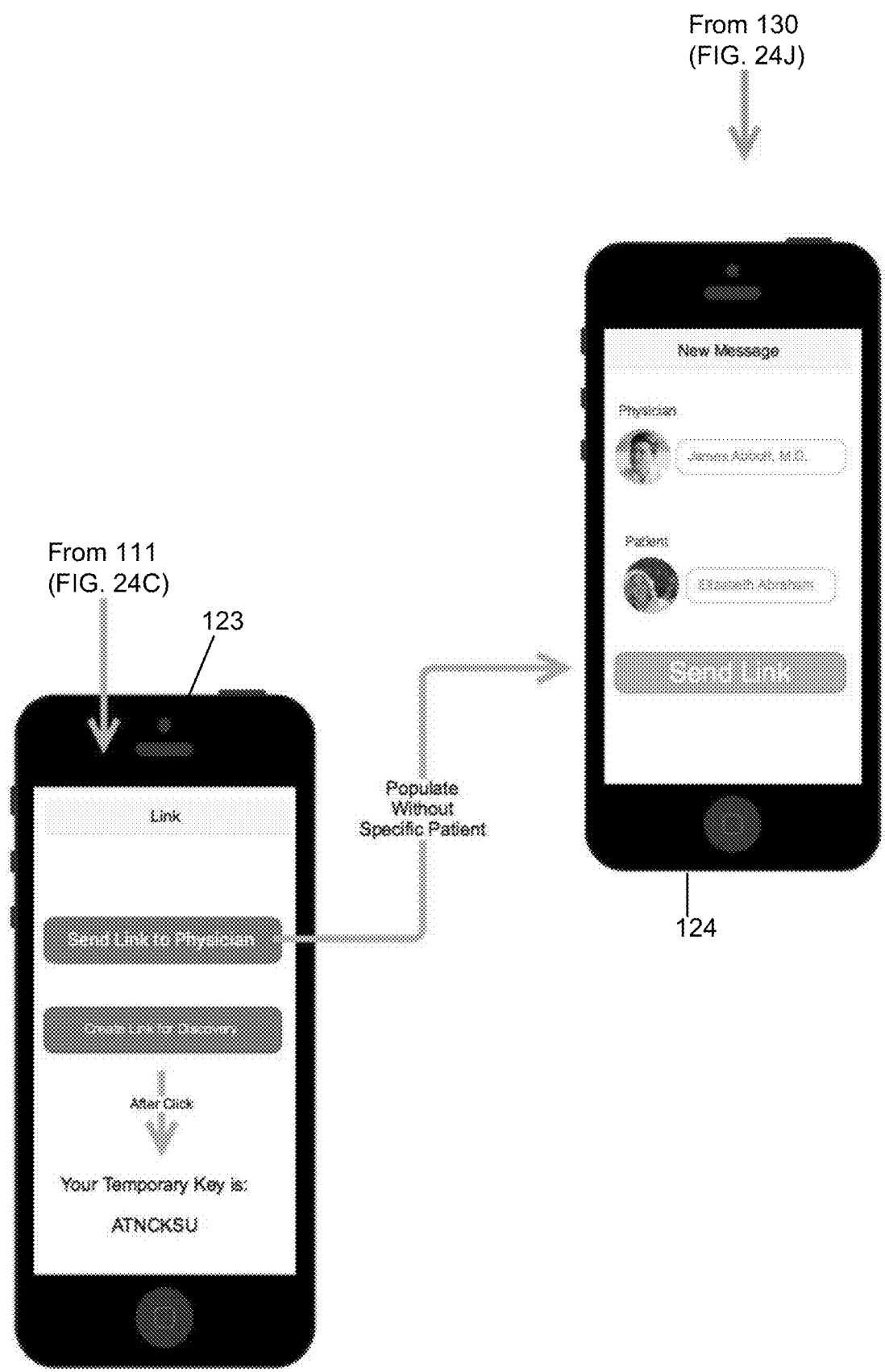
Figure 24H:
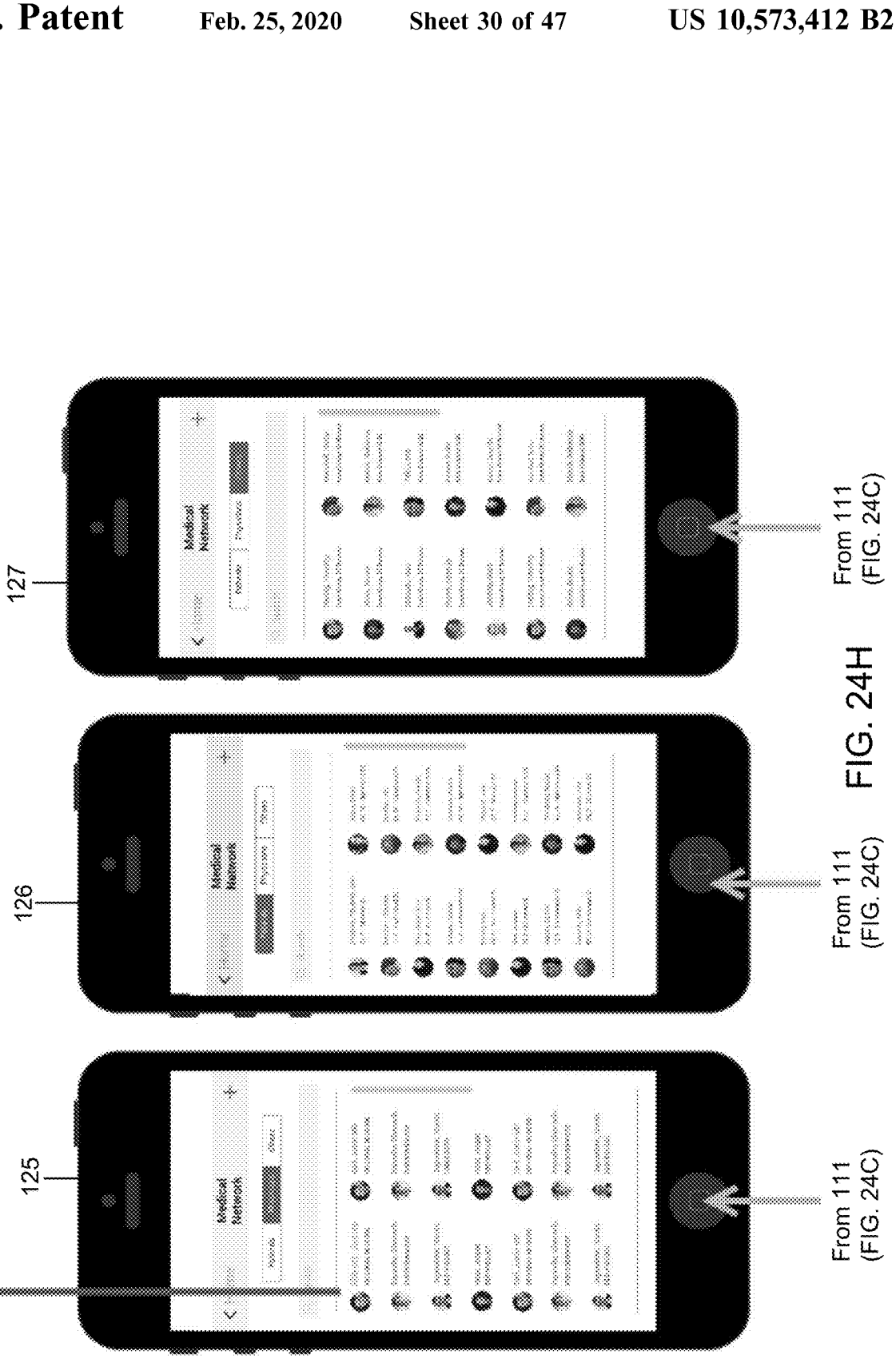
Figure 24I:
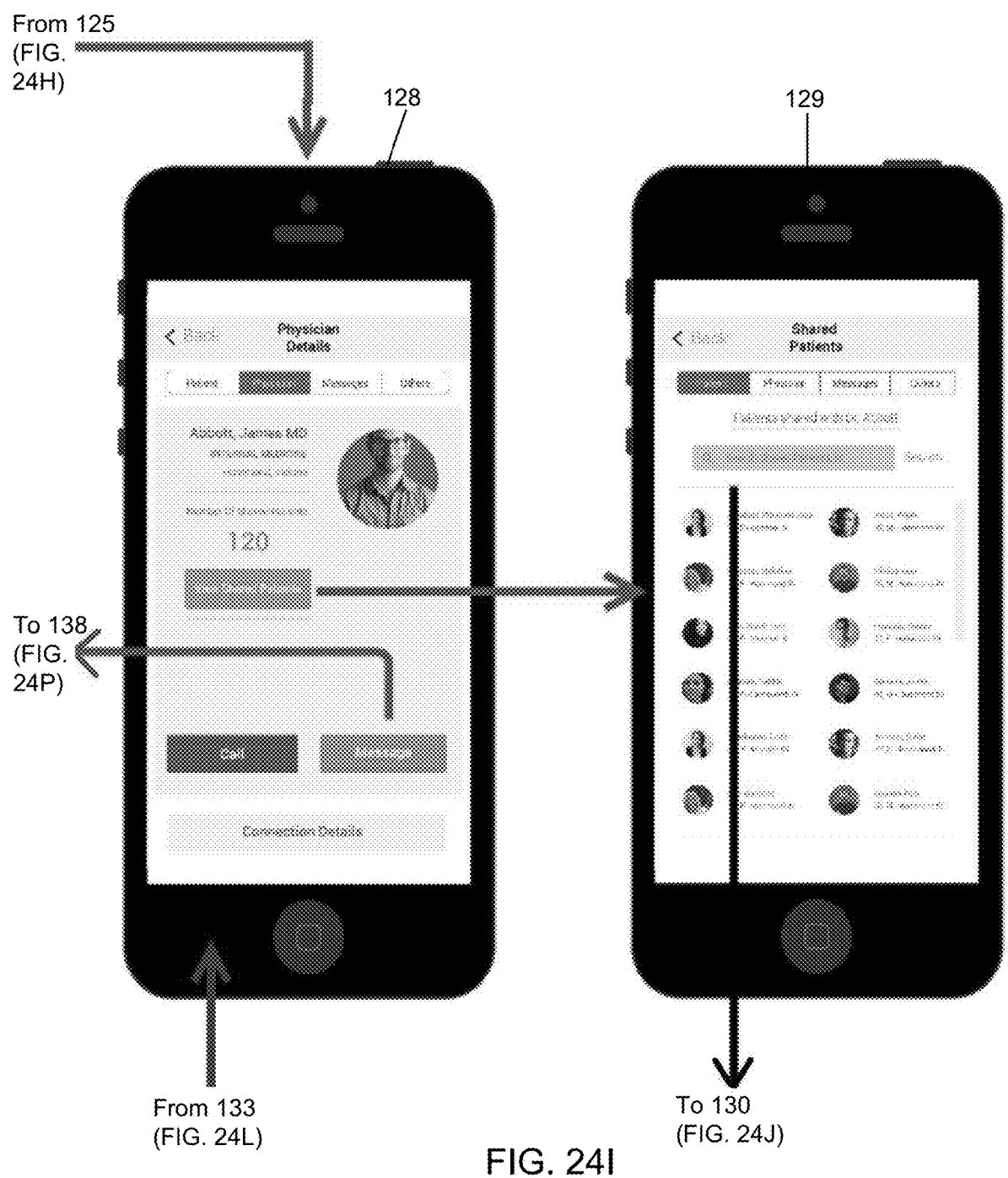
Figure 24J:
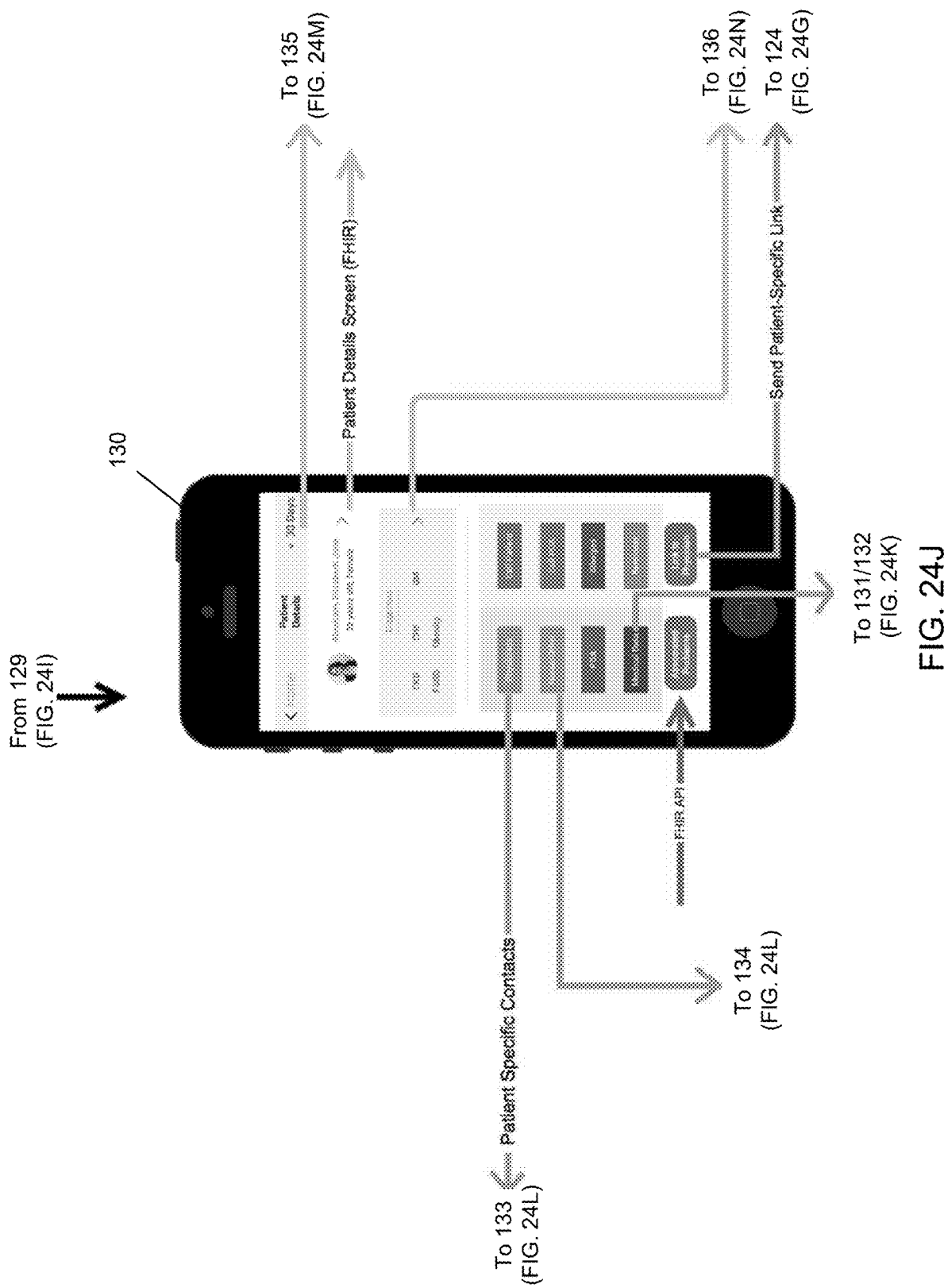
Figure 24K:
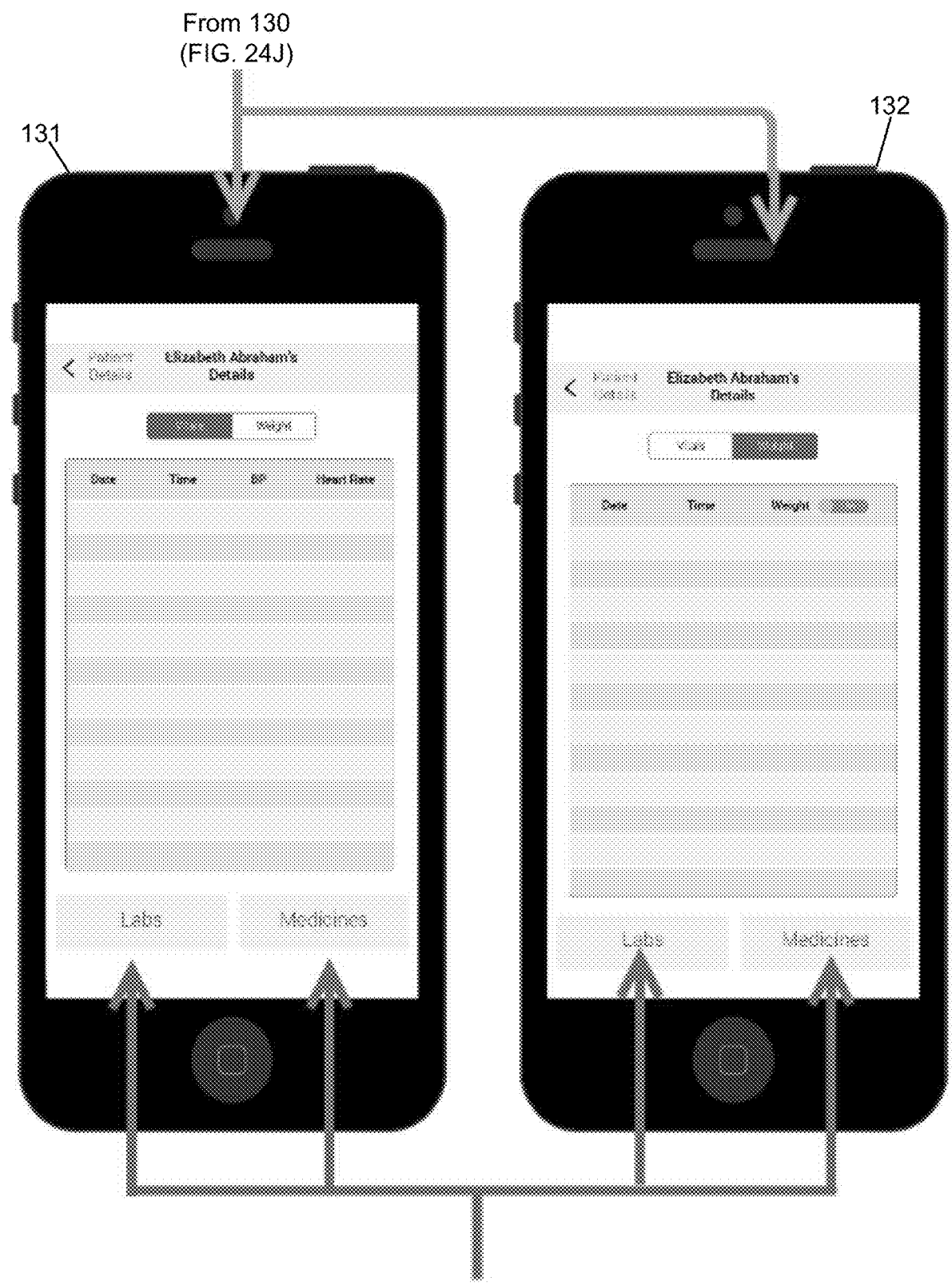
Figure 24L:
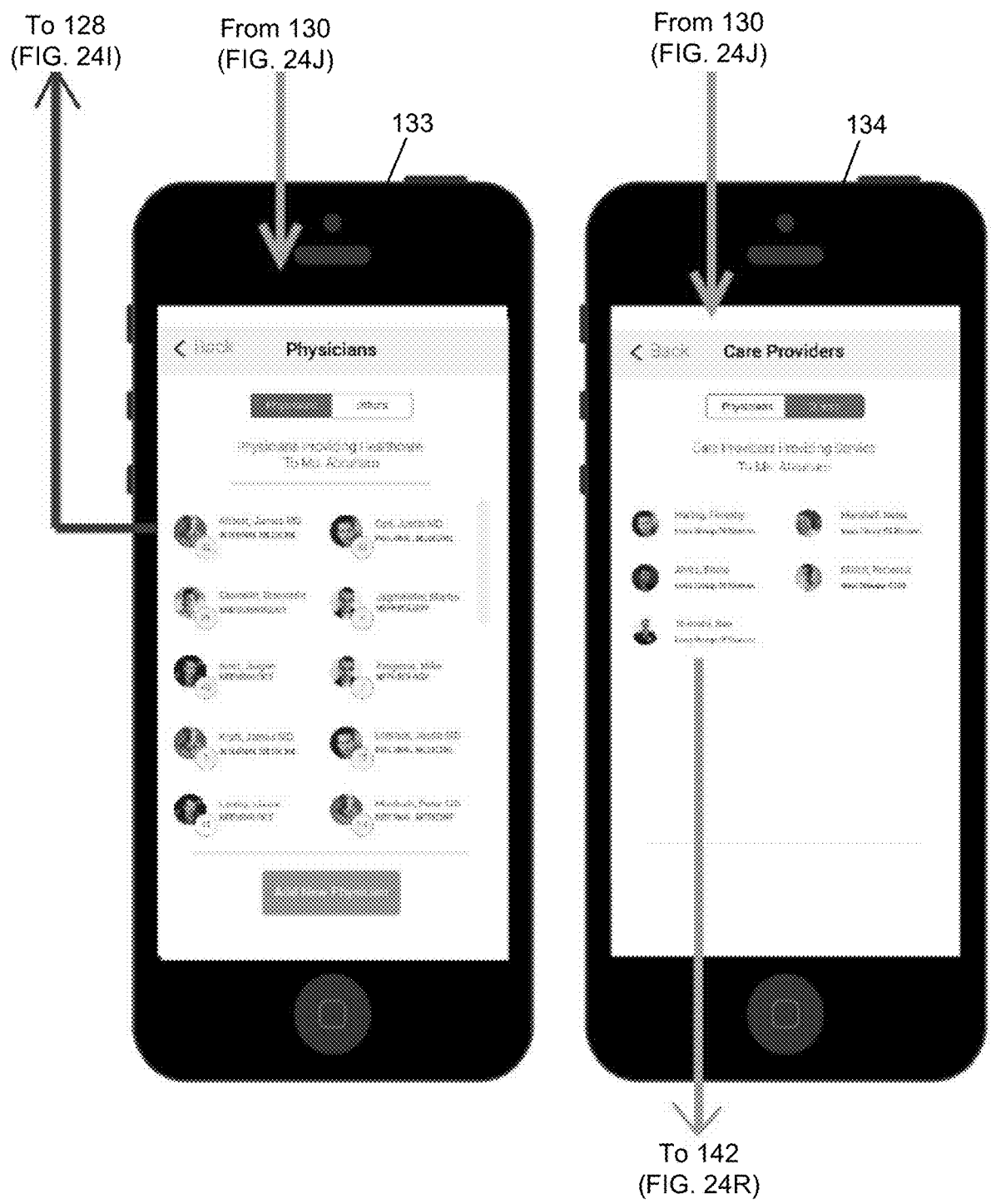
Figure 24M:
Figure 24N:
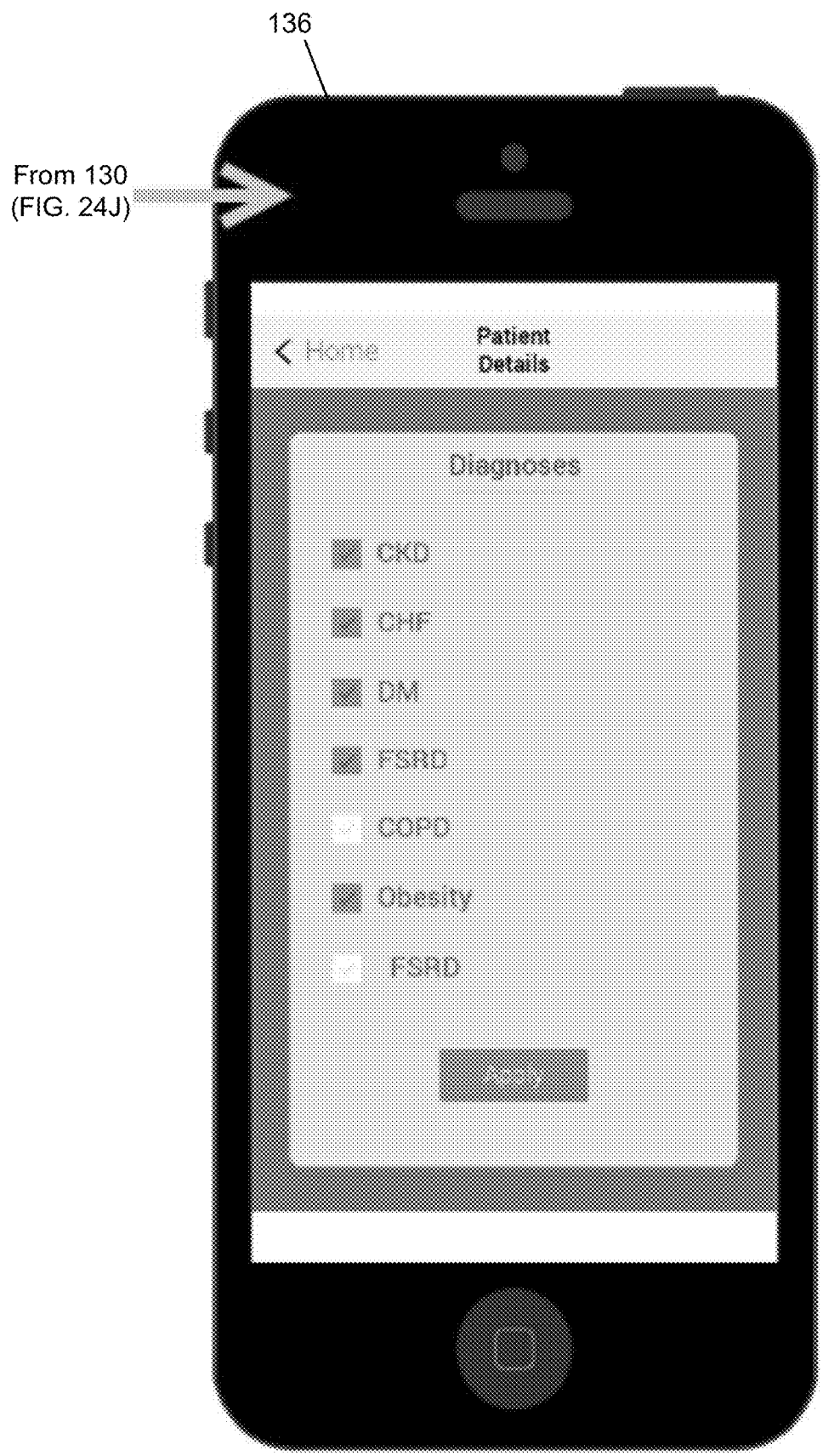

As shown in FIG. 24G (Screens 123 and 124), the user may add new physician or patient links to their network with the system by sending a secure link. This can be a link with a physician who may or may not share a patient with the user. The user's network, shown for example in FIG. 24H, can include physicians (Screen 125), patients (Screen 126) and other care providers (Screen 127). By selecting a physician, for example, from the list of physicians in the network, the user can access additional details about the physician, as seen in Screen 128 (FIG. 24I). This can include, for example, a description of the physician, the ability to call or message the physician and the ability to view commonly shared patients between the user and this physician (Screen 129). The user can select one of these patients to obtain more detailed information about the patient (Screen 130 (FIG. 24J)).

From the patient details screen (Screen 130 (FIG. 24J)), the user can access additional information about a particular patient. The user can access medical data such as a history for vitals (Screen 131, FIG. 24K) or weight history (Screen 132, FIG. 24K). Additional information, such as information about labs or medicines can further be accessed by calling an FHIR API ("Fast Healthcare Interoperability Resources Application Programming Interface") on other electronic health records or health information exchange, input by a third party. The records may be accessible by the secure server of the present application, and provided to the authorized user of the application for a specific patient using a secure, access authorization. The user may also access the patient's other linked physician contacts (Screen 133, FIG. 24L) and other linked care provider contacts (Screen 134, FIG. 24L). Additional details for a care provider can be accessed, shown for example in Screen 142 of FIG. 24R, by selecting a care provider. The user can access hospitalization discharge information (Screen 135, FIG. 24M) and diagnostic information (Screen 136, FIG. 24N) for the patient.

Figure 24O:
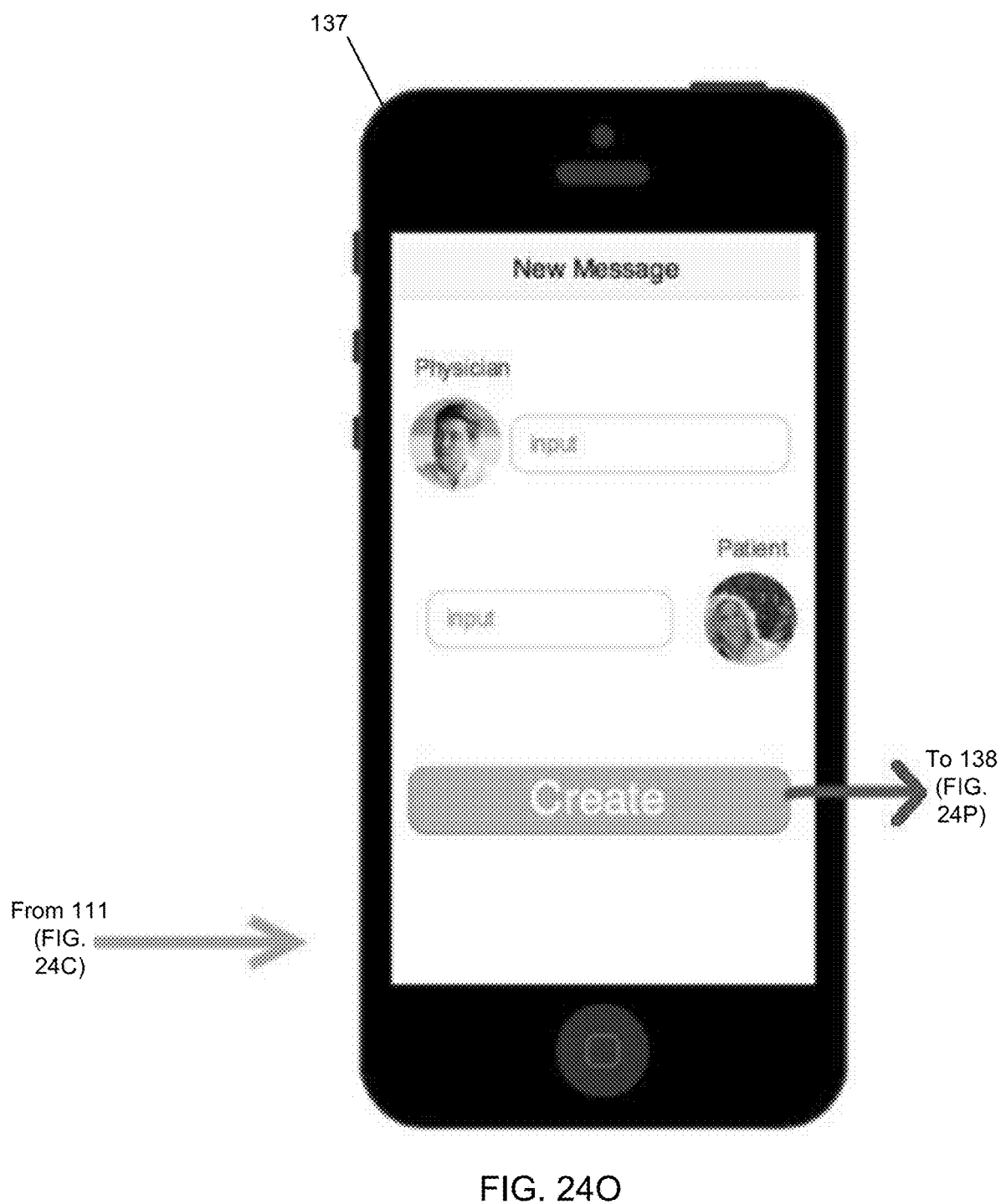
Figure 24P:
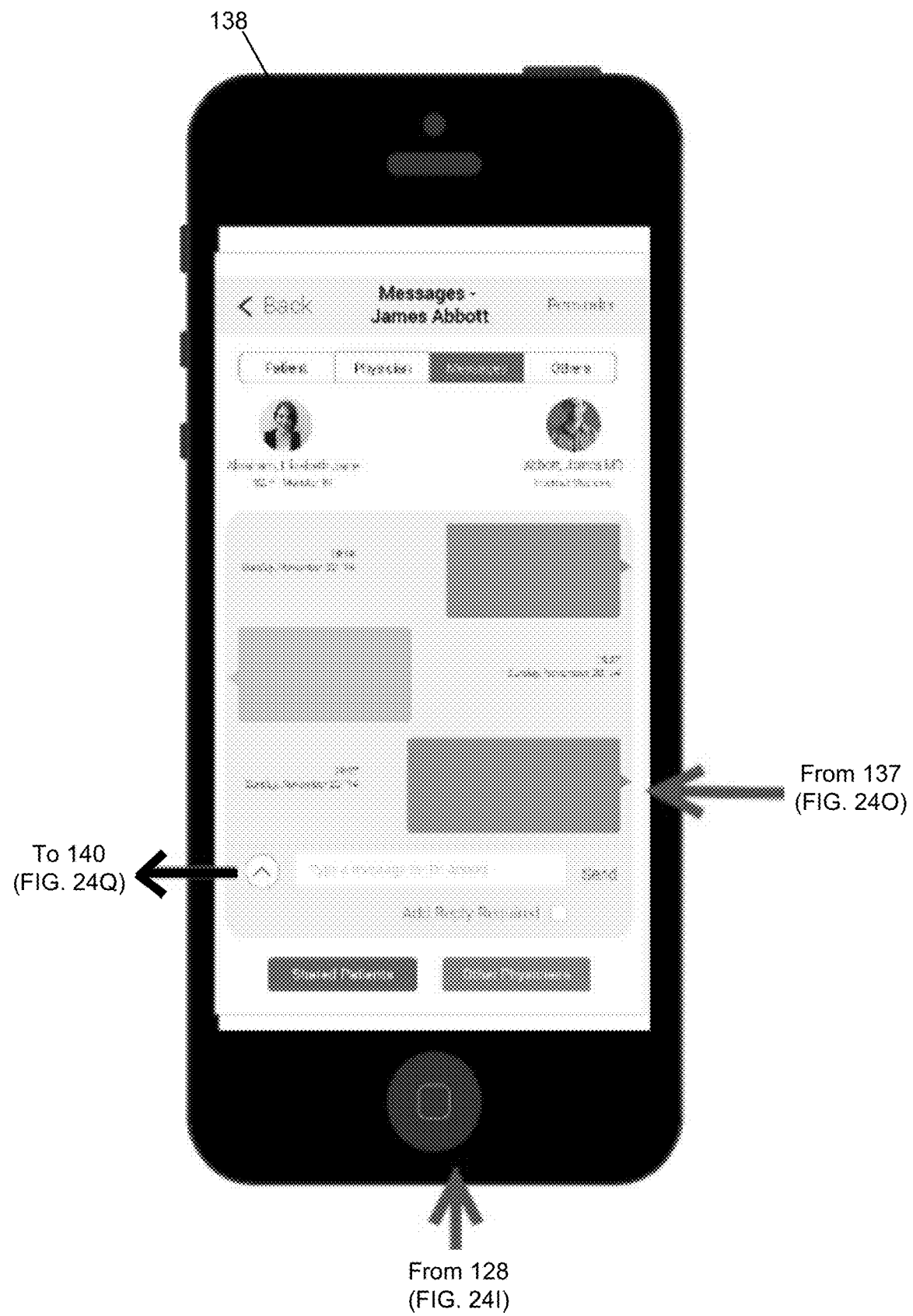
Figure 24Q:
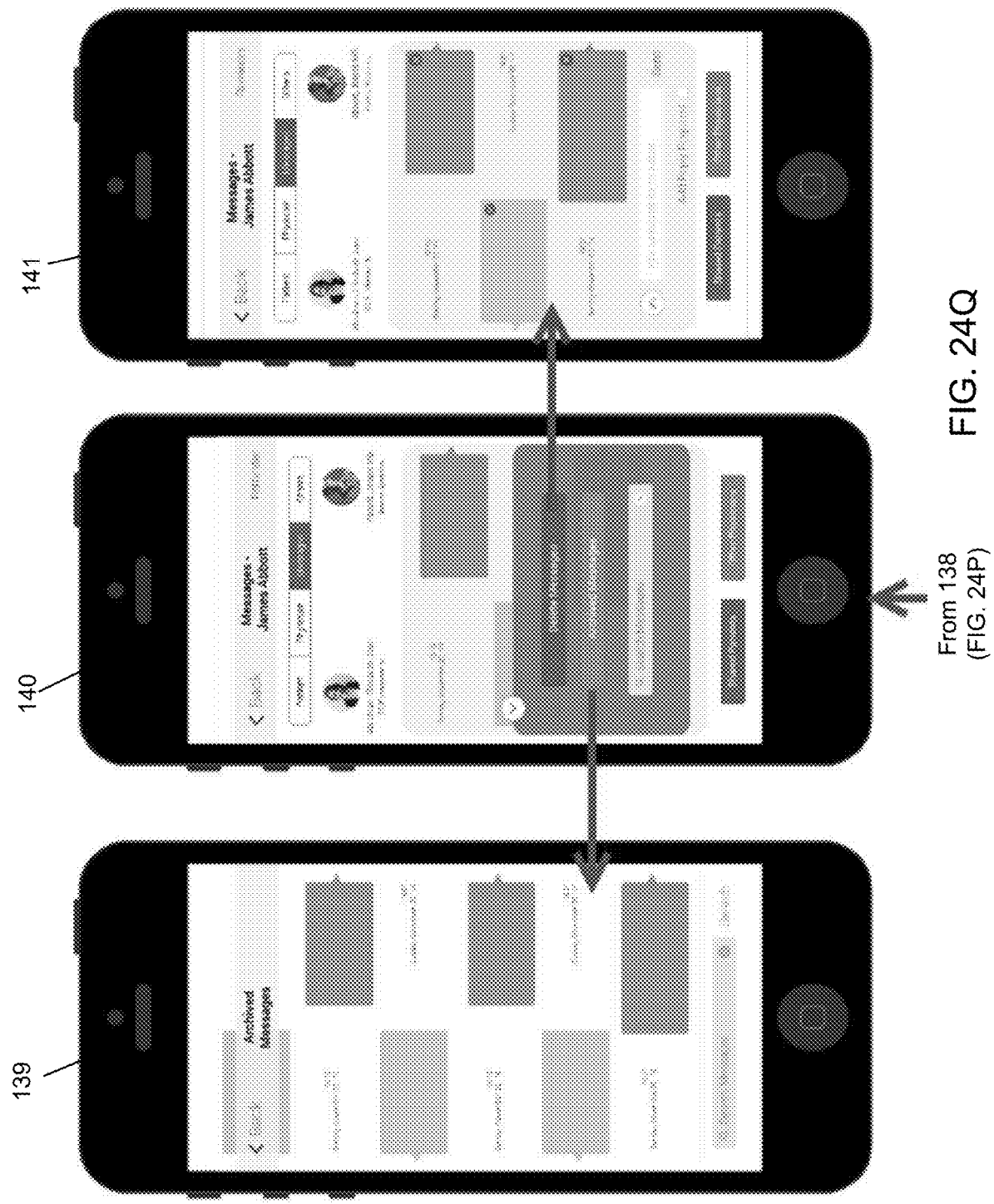
Figure 24R:
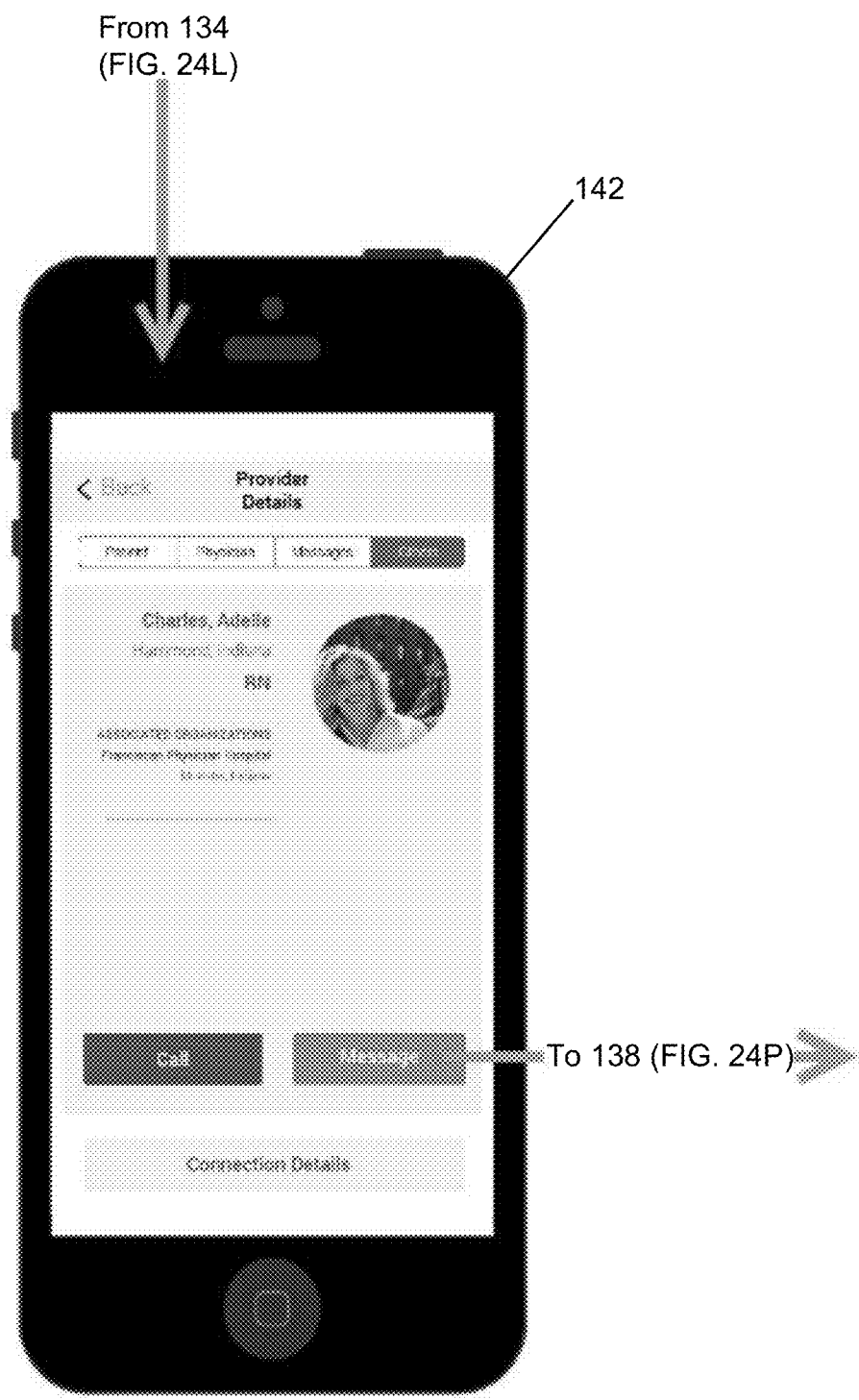

The user can further use the system to exchange messages with a specific patient's physician or care provider, as shown in Screens 137 and 138 of FIGS. 24O and 24P. These messages can be archived or deleted, shown for example in Screens 139-141 of FIG. 24Q.

Figure 25A:
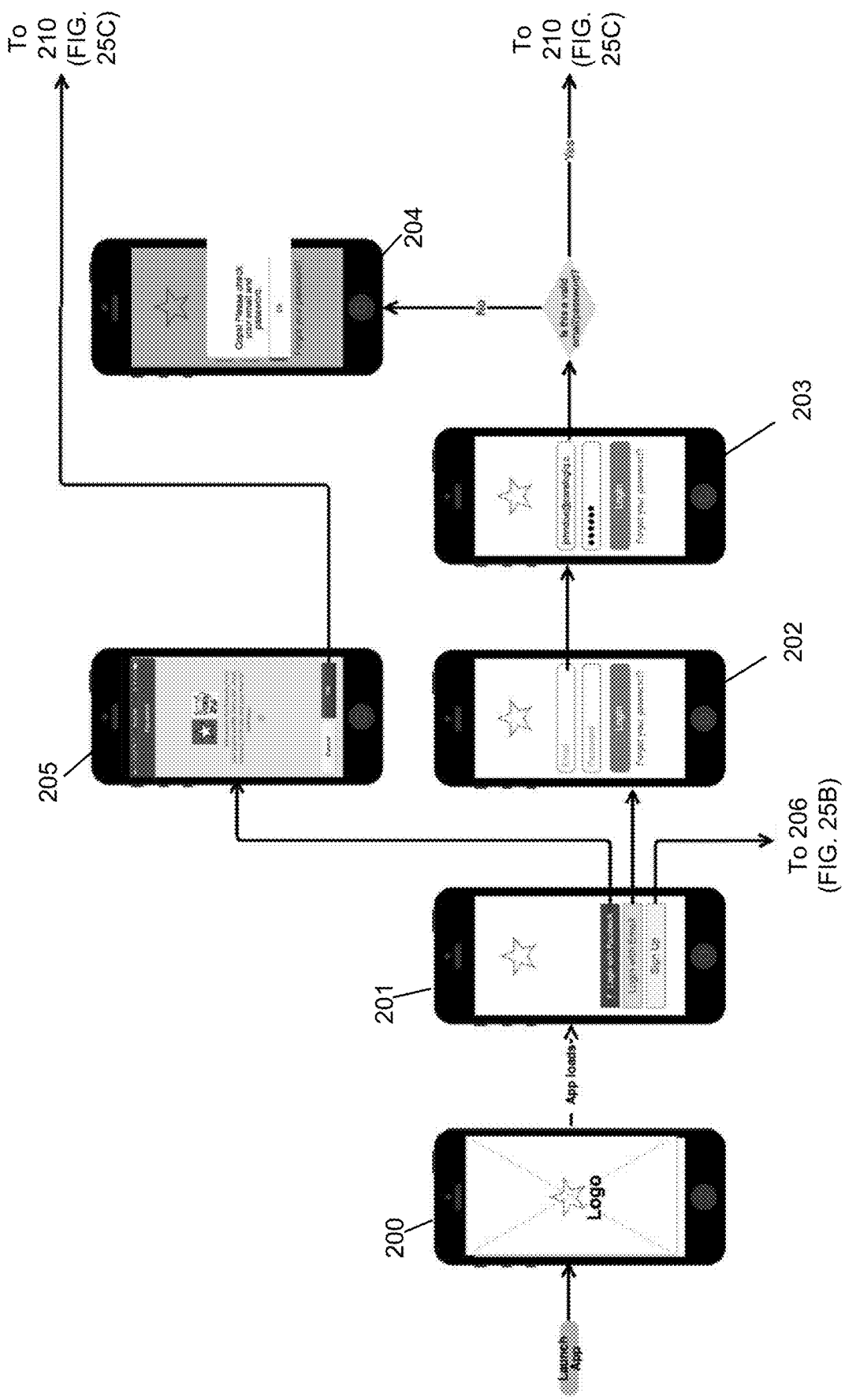
FIGS. 25A-25G show a flow chart showing operation of a second embodiment of the present invention and, in particular, various application screen from the patient-side implementation of the present invention.
Figure 25B:
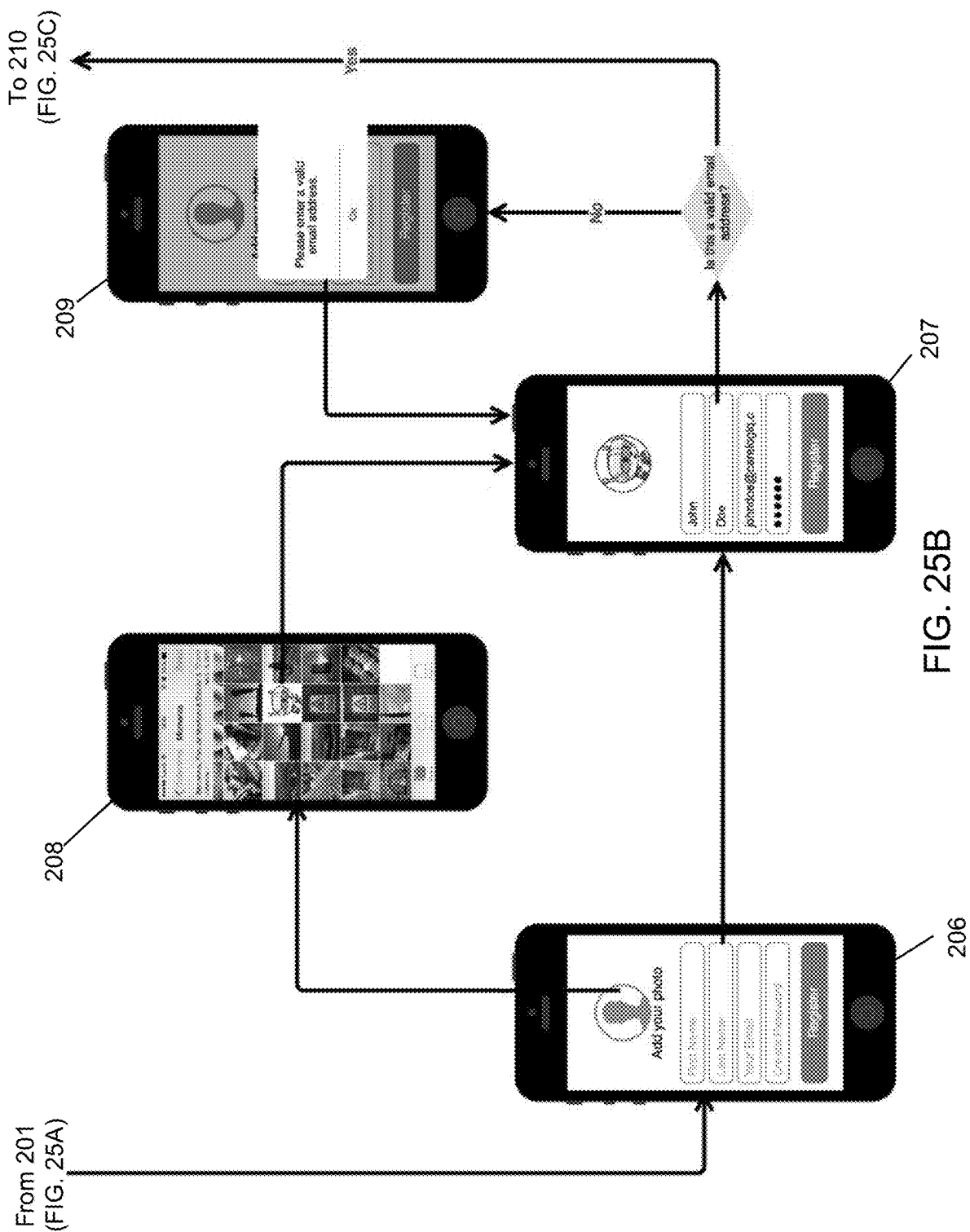

In FIG. 25A, Screens 200-205 show the launching of the system from the patient side and an example of a manner for accessing the system. If a user/patient is accessing the system for the first time, the user may establish an account with a user name and password for accessing the system, as shown in Screens 206-209 in FIG. 25B. After setting up a user account with a valid email address, the user can enter verifying information such as name date of birth, address, and social security number. After entering this information, an email can be sent to the user for validation to validate the user account. If an invalid email address or password is provided, then the user can be directed to attempt a further log-in, set up a new account, or provide verifying information to change the user's password or confirm email address. The screens for establishing an account further include the ability for the user to add personal information to accompany their account.

Figure 25C:
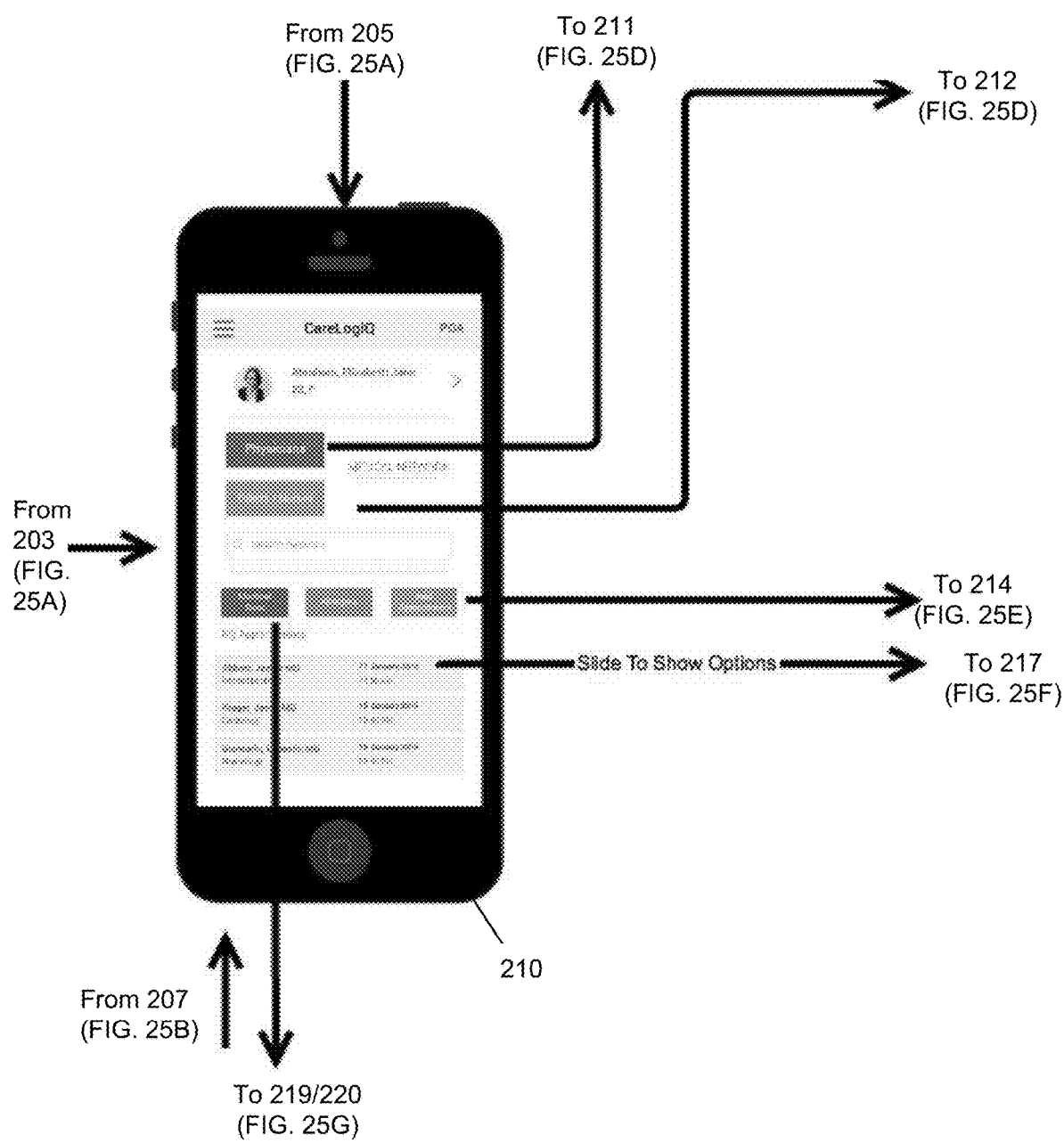
Figure 25D:
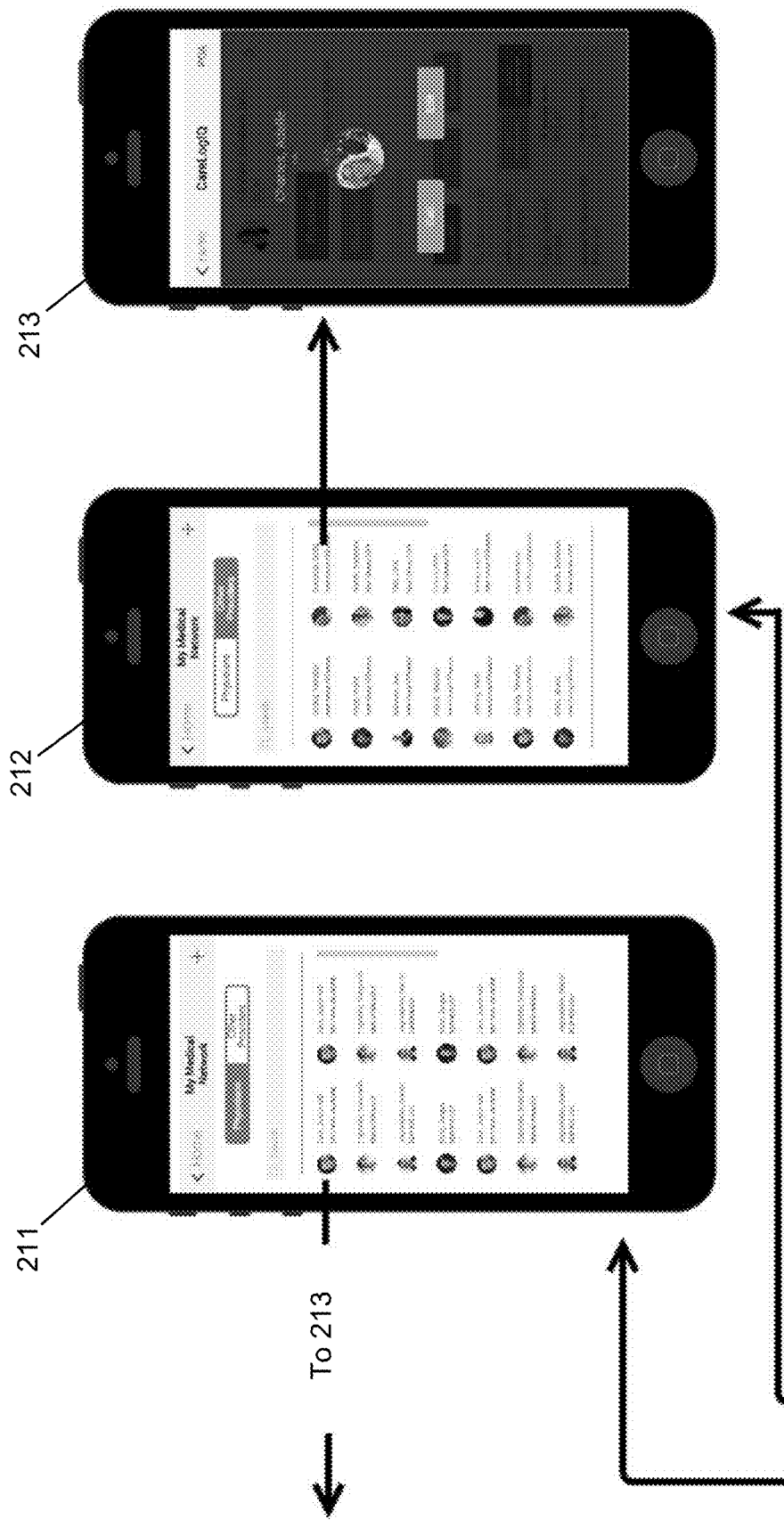
Figure 25E:
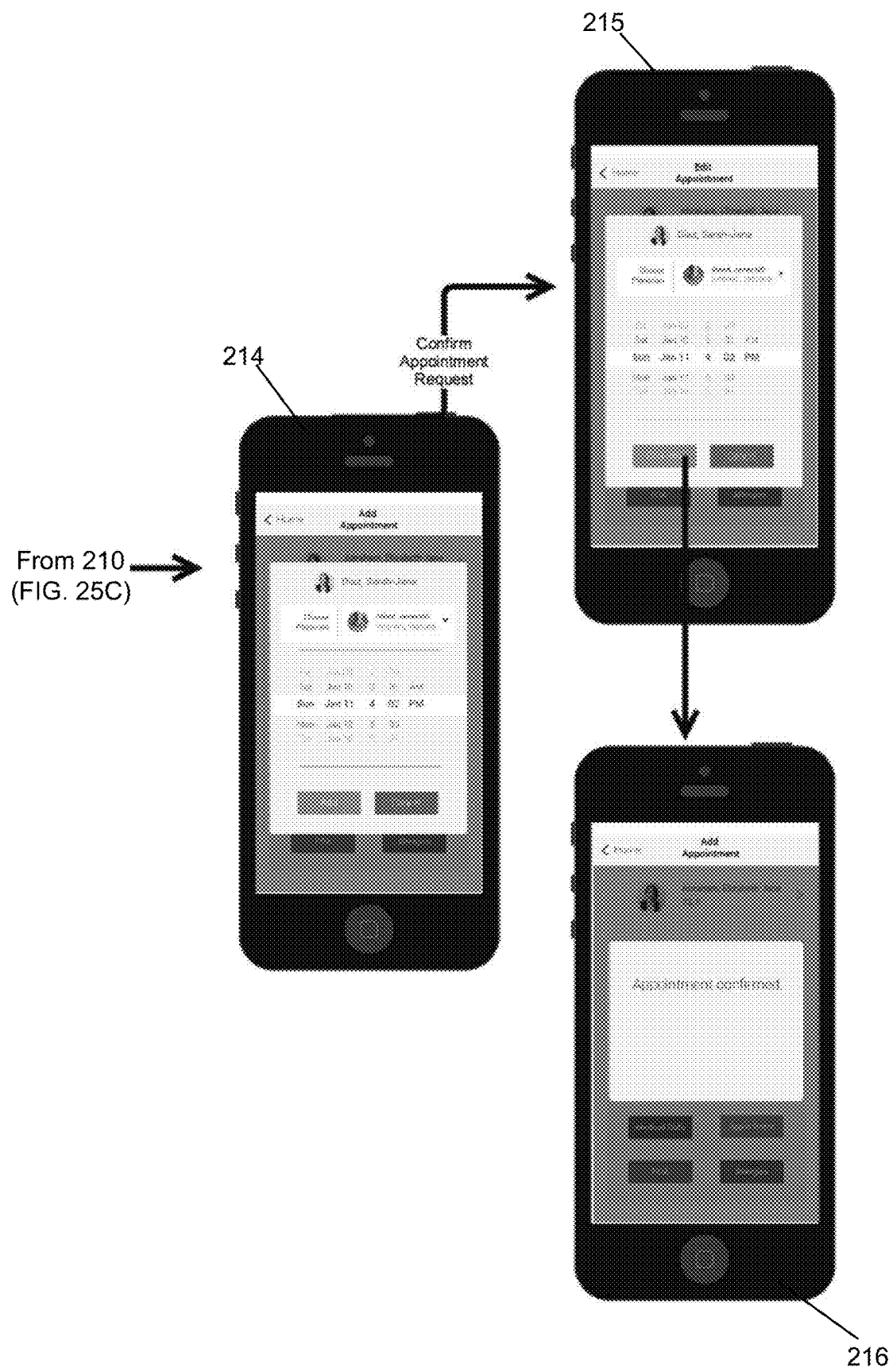
Figure 25F:
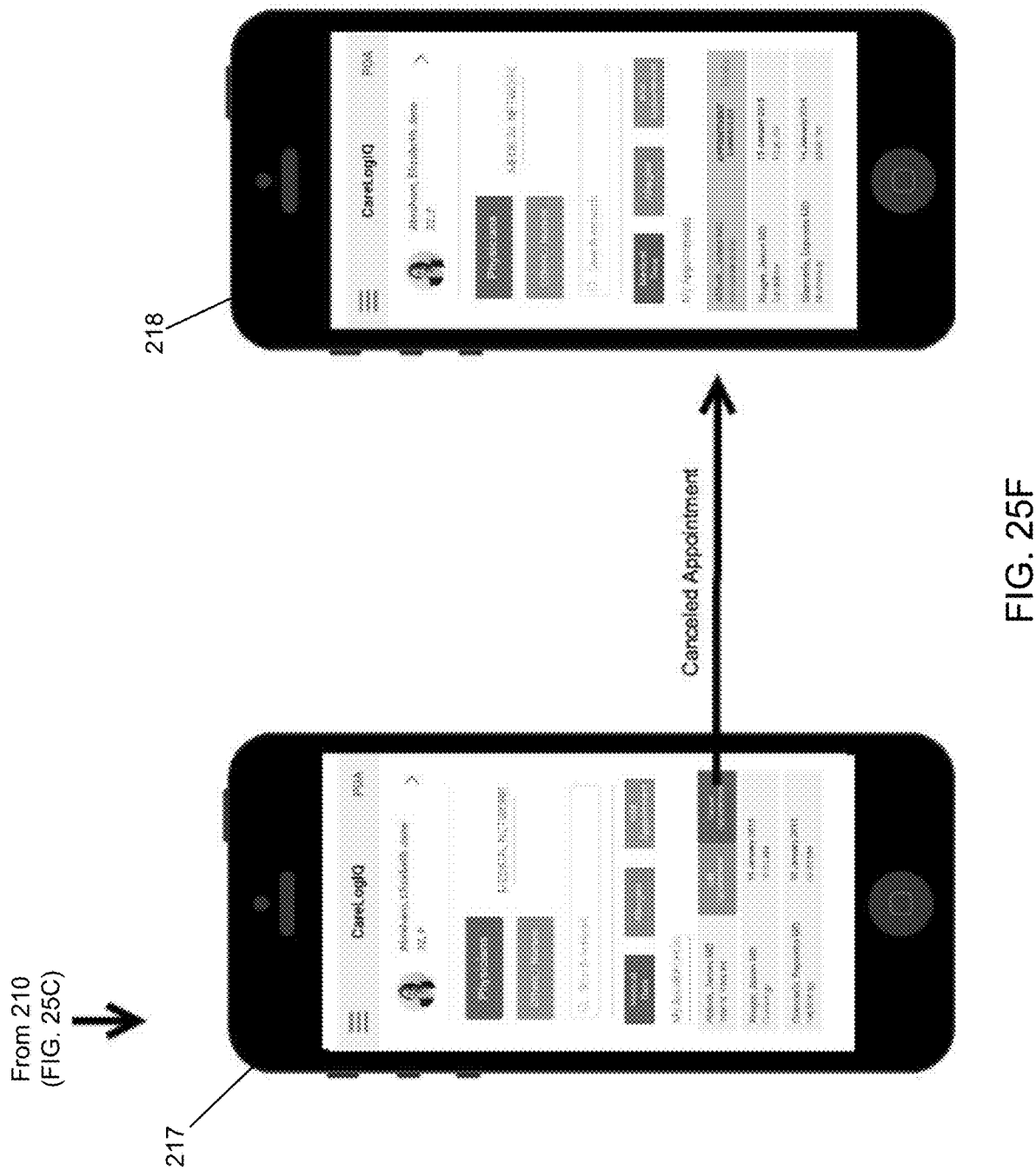

Screen 210, shown in FIG. 25C, depicts a patient home screen with aggregated notifications for the user. From this screen, the user can access his or her network of other physicians (Screen 211, FIG. 25D) or other care providers (Screen 212, FIG. 25D). The user can edit information for a physician or care provider, as shown in Screen 213 (FIG. 25D). The user can also create, view and edit any appointments they have from the home screen. Screens 214-216 (FIG. 25E) diagram the one example of the creation of an appointment, in which the user can select a physician and a time for the appointment and confirm the appointment. After an appointment has been created, it can be edited or deleted, as shown in Screens 217 and 218 (FIG. 25F).

Figure 25G:
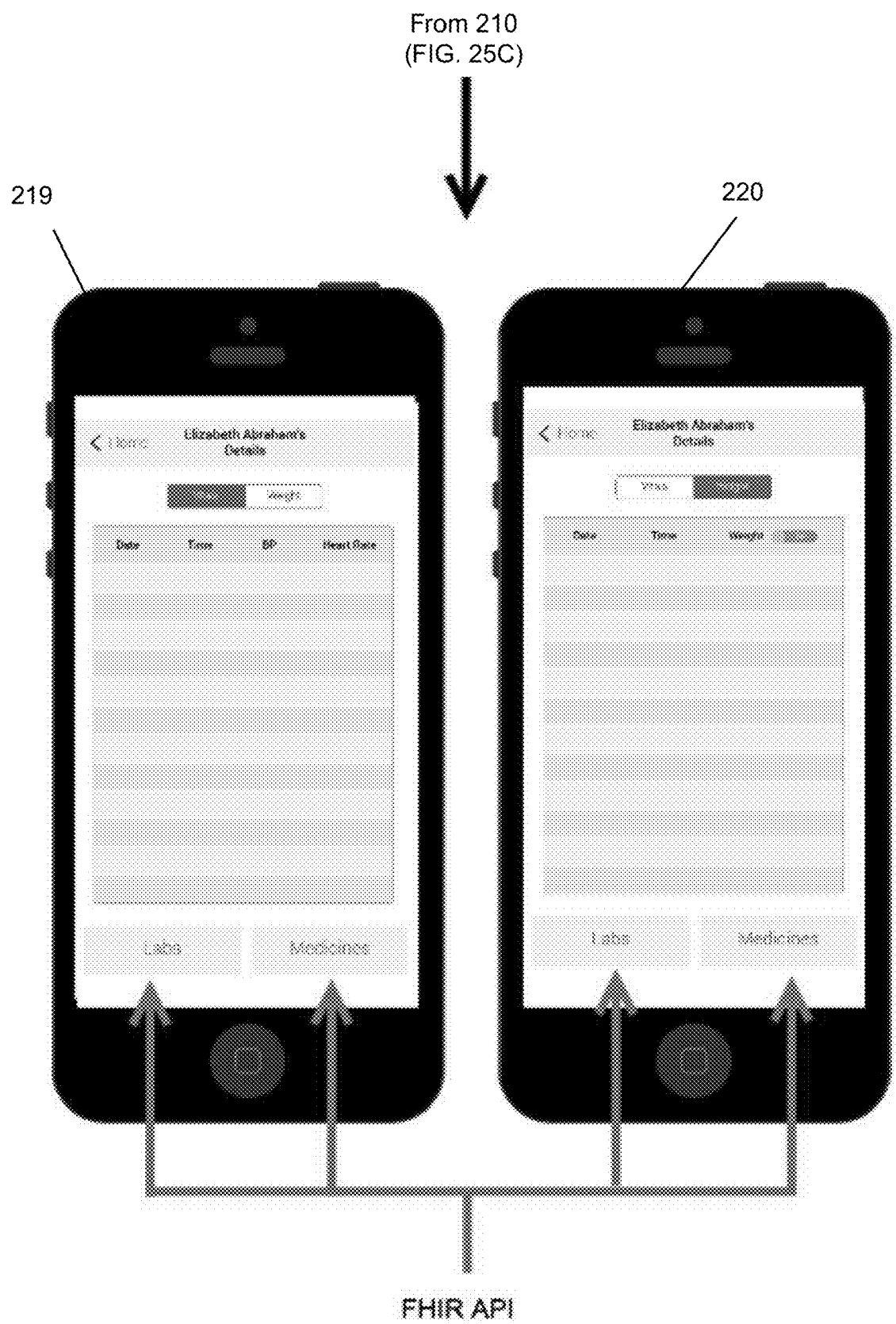

The user can access his or her own medical data such as a history for vitals (Screen 219, FIG. 25G) or weight history (Screen 220, FIG. 25G). Additional information, such as about labs or medicines, can further be provided through an FHIR API.

While there have been shown and described and pointed out fundamental novel features of the invention as applied to preferred embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto. Furthermore, in the claims means-plus-function clauses are intended to cover the structures described herein as performing the recited function and not only structural equivalents, but also equivalent structures.

What is claimed is:

1. A patient-centered communication system comprising:
a server comprising a processor, and a memory;

at least one physician device comprising:
  a processor,
  a memory including computer program code, the memory and the computer program code configured to, with the processor, cause the at least one physician device to perform:
    displaying a physician main menu with at least one selectable button to view patient information regarding at least one patient for which a physician provides care,
    displaying at least one selectable button to view the identity of one or more physicians also providing care to said at least one patient,
    displaying at least one selectable button to communicate with any one of the identified physicians, and
    providing a degree of linking between the physician associated with the system and other physicians in a network of the physician, wherein the degree of linking includes common/shared patients, non-common patients that are linked to at least one other physician who is linked to the physician associated with the at least one physician device, and patients linked by other physicians linked to the physician with the at least one physician device, and
    displaying a listing of physicians in the physician's network and sorting the listing of physicians by the degree of linking of each physician, wherein a user selectable button is provided to sort the listing of physicians by the degree of linking; and
at least one patient device comprising:
  a processor,
  a memory including computer program code, the memory and the computer program code configured to, with the processor, cause the at least one patient device at least to perform:
    displaying a patient main menu with at least one selectable button to view patient information and identified physicians for the patient; and
    displaying at least one selectable button to communicate with any one of the identified physicians for the patient.

2. The patient-centered communication system according to claim 1, wherein each of said at least one selectable buttons to communicate with any one of the identified physicians includes specific buttons associated with specific type of communication techniques.

3. The patient-centered communication system according to claim 2, wherein the specific types of communications include one or more of the following: telephone communication, video communication, text message communication, scheduled future communications, and prior communication information.

4. The patient-centered communication system according to claim 1, wherein the at least one physician device is further configured to identify all of the common patients between two physicians.

5. The patient-centered communication system according to claim 1, wherein the at least one physician device is further configured to display third party patient information to the physician associated with the at least one physician device.

6. The patient-centered communication system according to claim 1, further wherein the at least one physician device is configured to display patient information generated by the patient to the physician associated with the at least one physician device.

7. The patient-centered communication system according to claim 1, wherein the server, the at least one physician device, and the at least one patient device each comprise at least one transmitter and at least one receiver, and wherein the server is configured to send and receive information to and from each of the at least one physician device and the at least one patient device.

8. A method for providing a patient-centered communication system to a user having a user device comprising:
  providing a medical information and communication application to a user for installation on a user device, wherein the user device is a mobile device or a computer device and comprises a memory configured to store the application, a processor configured to execute the application, a display configured to display the executed application, a user interface configured to allow the user to operate the executed application, a transmitter and a receiver;
  providing medical information pertaining to a patient and storing said medical information on a server comprising a processor and a memory; wherein access to the stored medical data is restricted to the patient and linked third party users;
  generating a link request from said user and transmitting said link request to the patient having a second user device, wherein said link request is a request that the user become a linked third party user;
  receiving a verification of acceptance of the link request by the patient and authorizing the user to become a linked third party user;
  transmitting a request from the user device to the server for the medical information to be transmitted to the user device; and
  receiving the medical information by the user device for viewing by said user in said application on said user device; wherein the method further comprises:
  providing a degree of linking between the user and other linked third party users, wherein the degree of linking includes common/shared patients, non-common patients that are linked to at least one other user who is linked to the user associated with the user device, and patients linked by other users linked to the user; and
  displaying a listing of other linked third party users and sorting the listing by the degree of linking of each linked third party user, wherein a user selectable button is provided to sort the listing of other linked third party users by the degree of linking.

9. The method of claim 8, wherein the linked third party users include a plurality of physicians or health professionals, and the medical information received by the user comprises a list of the linked third party users.

10. The method of claim 8, further comprising sending and/or receiving communications within said application executed on the user device, to or from the patient.

11. The method of claim 9, further comprising sending and/or receiving communications within said application executed on the user device, to or from one or more of the linked third party users.

12. The method according to 9, further comprising:
  generating a plurality of further link requests from said user and transmitting said link requests to a plurality of further patients, each having a user device, and
  receiving a verification of acceptance of one or more of the plurality of link requests by one or more of the plurality of further patients and authorizing the user to become a linked third party user for the one or more of the plurality of further patients;

wherein the user becomes a linked third party user for a plurality of patients, each having medical information stored on said server.

13. The method according to claim 12, further comprising receiving information within the application relating to one or more of the plurality of physicians or health professionals, including a list of patients who have authorized both the user and the one or more of the plurality of physicians or health professionals to be linked third party users.

14. The method according to claim 8, further comprising updating the medical information for the patient and transmitting the updated medical information to the server.

15. The method according to claim 8, further comprising scheduling an event or notification relating to the patient, and transmitting a reminder message relating to the event or notification to the second user device at the scheduled time.

16. The patient-centered communication system according to claim 1, wherein the at least one physician device includes one or more of a mobile device or a computer device and the at least one patient device include one or more of a mobile device or a computer device.

17. A patient-centered communication system comprising:

at least one physician device comprising:
- a processor,
- a memory including computer program code, the memory and the computer program code configured to, with the processor, cause the at least one physician device to perform:
  - displaying a physician main menu with at least one selectable button to view patient information regarding at least one patient for which a physician provides care,
  - displaying at least one selectable button to view the identity of one or more physicians also providing care to said at least one patient,
  - displaying at least one selectable button to communicate with any one of the identified physicians,
  - providing a degree of linking between the physician associated with the system and other physicians in a network of the physician, wherein the degree of linking includes common/shared patients, non-common patients that are linked to at least one other physician who is linked to the physician associated with the at least one physician device, and patients linked by other physicians linked to the physician with the at least one physician device; and
  - displaying a listing of physicians in the physician's network and sorting the listing of physicians by the degree of linking of each physician, wherein a user selectable button is provided to sort the listing of physicians by the degree of linking;

wherein the at least one physician device includes one or more of a mobile device or a computer device.

18. The patient-centered communication system according to claim 17, wherein each of said at least one selectable buttons to communicate with any one of the identified physicians includes specific buttons associated with specific type of communication techniques; and wherein the specific types of communications include one or more of the following: telephone communication, video communication, text message communication, scheduled future communications, and prior communication information.

19. The patient-centered communication system according to claim 17, wherein the at least one physician device is further configured to display third party patient information to the physician associated with the at least one physician device.

20. The patient-centered communication system according to claim 1, wherein the computer program code executed by the processor of the at least one patient device is further configured to cause the at least one patient device at least to perform:

displaying medical information pertaining to the user of the at least one patient device, said medical information comprising customized guidance for the user, determined from collected health data pertaining to the user.

* * * * *